United States Patent
Cosford et al.

(10) Patent No.: US 6,774,138 B2
(45) Date of Patent: Aug. 10, 2004

(54) THIAZOLYL(PYRIDYL)ETHYNE COMPOUNDS

(75) Inventors: Nicholas David Peter Cosford, San Diego, CA (US); Leo Solomon Bleicher, La Jolla, CA (US); Jean-Michel Andre Vernier, San Diego, CA (US); Rowena V. Cube, San Diego, CA (US); Edwin Schweiger, San Diego, CA (US); Ian McDonald, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/217,800

(22) Filed: Aug. 13, 2002

(65) Prior Publication Data

US 2003/0055247 A1 Mar. 20, 2003

Related U.S. Application Data

(63) Continuation-in-part of application No. 09/387,073, filed on Aug. 31, 1999, now abandoned.

(51) Int. Cl.[7] .................... C07D 277/22; C07D 277/24; C07D 213/16; C07D 417/06
(52) U.S. Cl. ....................... 514/326; 514/342; 514/365; 546/209; 546/269.7; 548/202
(58) Field of Search ............................ 546/209, 269.7; 548/202; 514/326, 342, 365

(56) References Cited

U.S. PATENT DOCUMENTS

4,990,520 A * 2/1991 Trybulski et al. ........... 514/326

FOREIGN PATENT DOCUMENTS

| WO | WO 96/03406 | 2/1996 |
| WO | WO 99/02497 | 1/1999 |
| WO | WO 01/16121 | * 3/2001 |

OTHER PUBLICATIONS

M. A. Varney et al., Brit. J. Pharmacology, 126(Supp.):248(1999).
Electronic Database Abstract 116:151700, C. Shih et al., J. Med. Chem., 35:1109–1116(1992).
Electronic Database Abstract 127:130445, M.D. Varney et al., J. Med. Chem., 40:2502–2524(1997).
M. A. Varney et al., J. Pharmacology and Exptl. Therapeutics, 290:170–181(1999).
F. Gasparini et al., Brit. J. Pharmacology, 126(Supp.):249(1999).

* cited by examiner

*Primary Examiner*—Deepak Rao
(74) *Attorney, Agent, or Firm*—David L. Rose; David Rubin

(57) ABSTRACT

In accordance with the present invention, there is provided a novel class of heterocyclic compounds. Compounds of the invention contain a substituted, unsaturated five, six or seven membered heterocyclic ring that includes at least one nitrogen atom and at least one carbon atom. The ring additionally includes three, four or five atoms independently selected from carbon, nitrogen, sulfur and oxygen atoms. The heterocyclic ring has at least one substituent located at a ring position adjacent to a ring nitrogen atom. This mandatory substituent of the ring includes a moiety (B), linked to the heterocyclic ring via a carbon-carbon double bond, a carbon-carbon triple bond or an azo group. The mandatory substituent is positioned adjacent to the ring nitrogen atom. Invention compounds are capable of a wide variety of uses. For example heterocyclic compounds can act to modulate physiological processes by functioning as agonists and antagonists of receptors in the nervous system. Invention compounds may also act as insecticides, and as fungicides. Pharmaceutical compositions containing invention compounds also have wide utility.

2 Claims, No Drawings

THIAZOLYL(PYRIDYL)ETHYNE COMPOUNDS

This application is a continuation-in-part of U.S. patent application Ser. No. 09/387,073, filed Aug. 31, 1999, now abandoned.

FIELD OF INVENTION

The present invention relates to novel heterocyclic compounds which contain a heterocylic ring bearing at least one substituent, linked together by a linker containing an acetylenic group, a vinylic group or an azo group. In addition, the present invention relates to pharmaceutical compositions containing novel invention compounds.

BACKGROUND OF THE INVENTION

Unsaturated heterocylic compounds find a wide variety of uses. For example, compounds of this class find uses as modulators of physiological processes that are mediated by ligand-activated receptors Receptors that are activated by ligands are located throughout the nervous, cardiac, renal, digestive and bronchial systems, among others. Therefore, in the nervous system, for example, heterocyclic compounds are capable of functioning as agonists or antagonists of receptors for neurotransmitters, neurohormones and neuromodulators. Ligand-activated receptors have been identified in a wide variety of species, including humans, other mammals and vertebrates as well as in invertebrate species. Therefore, compounds of this class are also able to modulate receptor-mediated processes throughout phylogeny and find uses in a wide variety of applications, e.g., as insecticides and fungicides.

Accordingly, there is a continuing need in the art for new members of this compound class.

BRIEF DESCRIPTION OF THE INVENTION

In accordance with the present invention, there is provided a novel class of heterocyclic compounds. Compounds of the invention contain a substituted, unsaturated five, six or seven membered heterocyclic ring that includes at least one nitrogen atom and at least one carbon atom. The ring additionally includes three, four or five atoms independently selected from carbon, nitrogen, sulfur and oxygen atoms. The heterocyclic ring has at least one substituent located at a ring position adjacent to a ring nitrogen atom. This mandatory substituent of the ring includes a moiety (B), linked to the heterocyclic ring via a carbon-carbon double bond, a carbon-carbon triple bond or an azo group. The mandatory substituent is positioned adjacent to the ring nitrogen atom.

Invention compounds are useful for a wide variety of applications. For example heterocyclic compounds can act to modulate physiological processes by functioning as agonists and antagonists of receptors in the nervous system. Invention compounds may also act as insecticides, and as fungicides. Pharmaceutical compositions containing invention compounds also have wide utility.

DETAILED DESCRIPTION OF THE INVENTION

In accordance with the present invention, there are provided compounds having the structure:

A—L—B or enantiomers, diastereomeric isomers or mixtures of any two or more thereof, or pharmaceutically acceptable salts thereof, wherein:

A is a 5-, 6- or 7-membered ring having the structure:

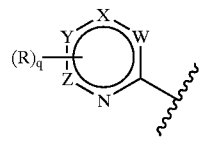

wherein at least one of W, X, Y and Z is $(CR)_p$, wherein p is 0, 1 or 2;

the remainder of W, X, Y and Z are each independently O, N or S; and each R is independently halogen, substituted or unsubstituted hydrocarbyl, substituted or unsubstituted aryl, heterocycle, mercapto, nitro, carboxyl, carbamate, carboxamide, hydroxy, ester, cyano, amine, amide, amidine, amido, sulfonyl or sulfonamide, wherein q is 0, 1, 2 or 3;

L is substituted or unsubstituted alkenylene, alkynylene, or azo; and

B is substituted or unsubstituted hydrocarbyl, substituted or unsubstituted cyclohydrocarbyl, substituted or unsubstituted heterocycle, optionally containing one or more double bonds, or substituted or unsubstituted aryl;

provided, that the following compounds are excluded:

the compounds wherein

A is a 6-membered ring wherein:

W, X, Y and Z are $(CR)_p$ wherein p is 1; and

R at the W position is hydrogen, lower alkyl, hydroxy, hydroxy-lower alkyl, amino-lower alkyl, lower alkylamino-lower alkyl, di-lower alkylamino-lower alkyl, unsubstituted or hydroxy-substituted lower alkyleneamino-lower alkyl, lower alkoxy, lower alkanoyloxy, amino-lower alkoxy, lower alkylamino-lower alkoxy, di-lower alkylamino-lower alkoxy, phthalimido-lower alkoxy, unsubstituted or hydroxy- or 2-oxo-imidazolidin-1-yl-substitued lower alkyleneamino-lower alkoxy, carboxy, esterified or amidated carboxy, carboxy-lower alkoxy or esterified carboxy-lower-alkoxy; R at the X position is hydrogen; R at the Y position is hydrogen, lower alkyl, carboxy, esterified carboxy, amidated carboxy, hydroxy-lower alkyl, hydroxy, lower alkoxy or lower alkanoyloxy; and R at the Z position is hydrogen, lower alkyl, hydroxy-lower alkyl, carboxy, esterified carboxy, amidated carboxy, unsubstituted or lower alkyl-, lower alkoxy-, halo- and/or trifluoromethyl-substituted N-lower alkyl-N-phenylcarbamoyl, lower alkoxy, halo-lower alkyl or halo-lower alkoxy;

L is substituted or unsubstituted alkenylene, alkynylene or azo,

B is substituted or unsubstituted aryl or heterocycle having two or more double bonds, wherein substituents are independently lower alkyl, lower alkenyl, lower alkynyl, phenyl, phenyl-lower alkynyl, hydroxy, hydroxy-lower alkyl, lower alkoxy, lower alkenyloxy, lower alkylenedioxy, lower alkanoyloxy, phenoxy, phenyl-lower alkoxy, acyl, carboxy, esterified carboxy, amidated carboxy, cyano, nitro, amino, acylamino, N-acyl-N-lower alkylamino, halo and halo-lower alkyl, wherein phenyl, phenyl-lower alkynyl, phenoxy, and phenyl-lower alkoxy may bear further substituents; and the compounds wherein
A is a 6-membered ring wherein:
W, X, Y and Z are $(CR)_p$ wherein p is 1; R at the X position is not hydrogen; and R at the W, Y and Z positions are hydrogen;
L is alkenylene or alkynylene; and
B is a substituted or unsubstituted aryl or heterocycle containing two or more double bonds; and the compounds wherein
A is a 5-membered ring wherein:
one of W, X, Y and Z is $(CR)_p$, and p is 0, two of W, X, Y and Z are $(CR)_p$ and p is 1, and the remaining variable ring member is O or S; or
one of W, X, Y and Z is N, one of W, X, Y and Z is $(CR)_p$ and p is 1, one of W, X, Y and Z is $(CR)_p$ and p is 0, and the remaining variable ring member is O, S or $(CR)_p$, and p is 1; or
two of W, X, Y and Z are N, one of W, X, Y and Z is $(CR)_p$, and p is 0, and the remaining variable ring member is, O or S or $(CR)_p$, and p is 1;
each R is independently hydrogen, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_3$–$C_6$-alkenyl or $C_3$–$C_8$-cycloalkyl;
L is alkynylene; and
B is substituted or unsubstituted aryl, wherein substituents are independently nitro, cyano, $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkoxycarbonyl, $C_3$–$C_6$-alkenyl, phenyl or phenoxy, wherein phenyl and phenoxy may bear further substituents; and the compounds wherein
A is a 6-membered ring wherein:
W, X, Y and Z are (CR)p, wherein p is 1 and R is hydrogen,
L is alkynylene; and
B is unsubstituted 1-cyclopenten-1-yl or unsubstituted 1-cyclohexen-1-yl; and the compounds wherein
A is a 5-membered ring wherein:
W is (CR)p, and p is 0, Y and Z are (CR)p, and p is 1, X is N or S; and R is phenyl; or
W is (CR)p, and p is 0, X and Z are (CR)p, and p is 1, Y is O, N or S; and R is phenyl;
L is unsubstituted alkenylene and
B is unsubstituted phenyl; and the compounds wherein A is a 5-membered ring containing two double bonds, wherein one of W, X, Y and Z is $(CR)_p$, and p is 0, and the remaining ring members are $(CR)_p$ and p is 1; and the compounds wherein A is unsubstituted heterocycle containing two or more double bonds; L is alkenylene or alkynylene, and B is unsubstituted phenyl.

In one aspect, this invention is directed to a compound having the structure:

A—L—B or enantiomers, diastereomeric isomers or mixtures of any two or more thereof, or pharmaceutically acceptable salts thereof, wherein B is substituted or unsubstituted pyridyl, thiazolyl, furyl, dihydropyranyl, dihydrothiopyranyl, or piperidinyl; wherein said substitution is by hydroxy, alkoxy, mercapto, aryl, halogen, trifluoromethyl, pentafluoroethyl, cyano, cyanomethyl, nitro, amino, amido, carboxamido, carbamido, esteryl, sulfonamido, or heterocyclyl other than tetrazolyl, triazolyl, dioxothiazolidinylidenyl, and oxothioxothiazolidinylidenyl.

In an embodiment of this one aspect, this invention is directed to a compound having the structure:

A—L—B or enantiomers, diastereomeric isomers or mixtures of any two or more thereof, or pharmaceutically acceptable salts thereof, wherein
A is 1,3-thiazol-2-yl, optionally substituted with halogen, substituted or unsubstituted hydrocarbyl, substituted or unsubstituted aryl, heterocyclyl, mercapto, nitro, carboxyl, carbamido, hydroxy, esteryl, cyano, amino, amido, or sulfonamide;
L is substituted or unsubstituted alkynylene; and
B is substituted or unsubstituted pyridyl, thiazolyl, furyl, dihydropyranyl, dihydrothiopyranyl, or piperidinyl;
wherein said substitution is by hydroxy, alkoxy, mercapto, aryl, halogen, trifluoromethyl, pentafluoroethyl, cyano, cyanomethyl, nitro, amino, amido, carboxamido, carbamido, esteryl, sulfonamido, or heterocyclyl other than tetrazolyl, triazolyl, dioxothiazolidinylidenyl, and oxothioxothiazolidinylidenyl.

As employed herein, "hydrocarbyl" refers to straight or branched chain univalent and bivalent radicals derived from saturated or unsaturated moieties containing only carbon and hydrogen atoms, and having in the range of about 1 up to 12 carbon atoms. Exemplary hydrocarbyl moieties include alkyl moieties, alkenyl moieties, dialkenyl moieties, trialkenyl moieties, alkynyl moieties, alkadiynyl moieties, alkatriynyl moieties, alkenyne moieties, alkadienyne moieties, alkenediyne moieties, and the like. The term "substituted hydrocarbyl" refers to hydrocarbyl moieties further bearing substituents as set forth below;

"alkyl" refers to straight or branched chain alkyl radicals having in the range of about 1 up to 12 carbon atoms; "substituted alkyl" refers to alkyl radicals further bearing one or more substituents such as hydroxy, alkoxy, mercapto, aryl, heterocycle, halogen, trifluoromethyl, pentafluoroethyl, cyano, cyanomethyl, nitro, amido, amide, amidine, amido, carboxyl, carboxamide, carbamate, ester, sulfonyl, sulfonamide, and the like;

"alkenyl" refers to straight or branched chain hydrocarbyl radicals having at least one carbon-carbon double bond, and having in the range of about 2 up to 12 carbon atoms (with radicals having in the range of about 2 up to 6 carbon atoms presently preferred), and "substituted alkenyl" refers to alkenyl radicals further bearing one or more substituents as set forth above;

"alkenylene" refers to straight or branched chain divalent alkenyl moieties having at least one carbon-carbon double bond, and having in the range of about 2 up to 12 carbon atoms (with divalent alkenyl moieties having in the range of about 2 up to 6 carbon atoms presently preferred), and "substituted lower alkenylene" refers to divalent alkenyl radicals further bearing one or more substituents as set forth above;

"alkynyl" refers to straight or branched chain hydrocarbyl radicals having at least one carbon-carbon triple bond, and having in the range of about 2 up to 12 carbon atoms (with radicals having in the range of about 2 up to 6 carbon atoms presently being preferred), and "substituted alkynyl" refers to alkenyl radicals further bearing one or more substituents as set forth above;

"alkynylene" refers to straight or branched chain divalent alkynyl moieties having at least one carbon-carbon triple bond, and having in the range of about 2 up to 12 carbon atoms (with divalent alkynyl moieties having two carbon atoms presently being preferred), and "substituted alkynylene" refers to divalent alkynyl radicals further bearing one or more substituents as set forth above;

"cyclohydrocarbyl" refers to cyclic (i.e., ring-containing) univalent radicals derived from saturated or unsaturated moieties containing only carbon and hydrogen atoms, and having in the range of about 3 up to 20 carbon atoms. Exemplary cyclohydrocarbyl moieties include cycloalkyl moieties, cycloalkenyl moieties, cycloalkadienyl moieties, cycloalkatrienyl moieties, cycloalkynyl moieties, cycloalkadiynyl moieties; spiro hydrocarbon moieties wherein two rings are joined by a single atom which is the only common member of the two rings (e.g., spiro[3.4]octanyl, and the like), bicyclic hydrocarbon moieties wherein two rings are joined and have two atoms in common (e.g., bicyclo[3.2.1]octane, bicyclo [2.2.1]hept-2-ene, and the like), and the like. The term "substituted cyclohydrocarbyl" refers to cyclohydrocarbyl moieties further bearing one or more substituents as set forth above;

"cycloalkyl" refers to ring-containing radicals containing in the range of about 3 up to 20 carbon atoms, and "substituted cycloalkyl" refers to cycloalkyl radicals further bearing one or more substituents as set forth above;

"cycloalkenyl" refers to ring-containing alkenyl radicals having at least one carbon-carbon double bond in the ring, and having in the range of about 3 up to 20 carbon atoms, and "substituted cycloalkenyl" refers to cyclic alcenyl radicals further bearing one or more substituents as set forth above;

"cycloalkynyl" refers to ring-containing alkynyl radicals having at least one carbon-carbon triple bond in the ring, and having in the range of about 3 up to 20 carbon atoms, and "substituted cycloalkynyl" refers to cyclic alkynyl radicals further bearing one or more substituents as set forth above;

"aryl" refers to mononuclear and polynuclear aromatic radicals having in the range of 6 up to 14 carbon atoms, and "substituted aryl" refers to aryl radicals further bearing one or more substituents as set forth above, for example, alkylaryl moieties;

"heterocycle" refers to ring-containing radicals having one or more heteroatoms (e.g., N, O, S) as part of the ring structure, and having in the range of 3 up to 20 atoms in the ring. Heterocyclic moieties may be saturated or unsaturated when optionally containing one or more double bonds, and may contain more than one ring. Heterocyclic moieties include, for example, monocyclic moieties such as imidazolyl moieties, pyrimidinyl moieties, isothiazolyl moieties, isoxazolyl moieties, and the like, and bicyclic heterocyclic moieties such as azabicycloalkanyl moieties, oxabicycloalkyl moieties, and the like. The term "substituted heterocycle" refers to heterocycles further bearin one or more substituents as set forth above;

"azo" refers to the bivalent moiety —N=N—, wherein each bond is attached to a different carbon atom;

"halogen" refers to fluoride, chloride, bromide or iodide radicals.

In accordance with the present invention, A is a 5-, 6- or 7-membered unsaturated heterocyclic moiety, containing a ring having at least one nitrogen atom located on the ring in a position adjacent to a carbon atom which bears a linking moiety as a substituent. The ring further contains 3, 4 or 5 independently variable atoms selected from carbon, nitrogen, sulfur and oxygen. Thus, A can be pyridinyl, imidazolyl, pyridazinyl, pyrimidinyl, pyrazoyl, pyrazinyl, triazolyl, triazinyl, tetrazolyl, tetrazinyl, isoxazolyl, oxazolyl, oxadiazolyl, oxatriazolyl, oxadiazinyl, isothiazolyl, thiazoyl, dioxazolyl, oxathiazolyl, oxathiazinyl, azepinyl, diazepinyl, and the like. Those of skill in the art will recognize that multiple isomers exist for a single chemical formula; each of the possible isomeric forms of the various empirical formulae set forth herein are contemplated by the invention. When a variable ring atom is carbon, it bears a hydrogen, or is optionally substituted with halogen, substituted or unsubstituted hydrocarbyl, substituted or unsubstituted aryl, thiol, nitro, carboxyl, ester, cyano, amine, amide, carboxamide, amidine, amido, sulfonamide, and the like, with presently preferred embodiments having no substituent (i.e., q is 0) or bearing the following substituents: halogen, alkyl, containing one up to four carbon atoms, fluorinated alkyl containing one up to four carbon atoms, and amine. Substitution at position Z of the ring is presently preferred.

In accordance with one embodiment of the invention, A is a 5-, 6- or 7-membered ring containing, as ring members, a nitrogen atom and a sulfur atom. Moieties contemplated for use by this embodiment of the invention include those wherein A is isothiazol-3-yl (1,2-thiazol-3-yl), thiazol-4-yl (1,3,-thiazolyl), thiazol-2-yl (1,3-thiazol-2-yl), 1,2-thiazin-3-yl, 1,3-thiazin-4-yl, 1,4-thiazin-3-yl 1,3-thiazin-2-yl, thiazepinyl, and the like. Presently preferred moieties include those wherein A is isothiazol-3-yl (1,2-thiazol-3-yl), thiazol-4-yl (1,3-thiazol-4-yl) and thiazol-2-yl (1,3-thiazol-2-yl).

In accordance with another embodiment of the invention, A is a 5-, 6- or 7-membered ring containing, as ring members, a nitrogen atom and an oxygen atom. Moieties contemplated by this embodiment of the invention include those wherein A is 1,2-oxazin-3-yl, 1,3-oxazin-4-yl, 1,4-oxazin-3-yl, 1,3-oxazin-2-yl, oxazol-2-yl, isoxazol-3-yl, oxazol-4-yl, oxazepinyl, and the like. Presently preferred moieties include those wherein A is oxazol-2-yl, isoxazol-3-yl and oxazol-4-yl.

In accordance with another embodiment of the invention, A is a 5-, 6-, or 7-membered ring containing as ring members two nitrogen atoms. Moieties contemplated by this embodiment of the invention include those wherein A is 3-pyridazinyl (1,2-diazin-3-yl), pyrimidin-4-yl (1,3-diazin-4-yl), pyrazin-3-yl (1,4-diazin-3-yl), pyrimidin-2-yl (1,3-diazin-2-yl), pyrazol-3-yl (1,2-diazol-3-yl), imidazol-4-yl (1,3-isodiazol-4-yl), imidazol-2-yl (1,3-isodiazol-2-yl), diazepinyl, and the like. Presently preferred moieties include those wherein A is 3-pyridazinyl (1,2-diazin-3-yl), pyrimidin-4-yl (1,3-diazin-4-yl), pyrazin-3-yl (1,4-diazin-3-yl), pyrimidin-2-yl (1,3-diazin-2-yl), 1,3-isodiazol-4-yl and 1,3-isodiazol-2-yl.

In accordance with still another embodiment of the invention, A is a 5-, 6-, or 7-membered ring containing, as ring members, three nitrogen atoms. Moieties contemplated by this embodiment of the invention include those wherein A is 1,2,3-triazin-4-yl, 1,2,4-triazin-6-yl, 1,2,4-triazin-3-yl, 1,2,4-triazin-5-yl, 1,3,5-triazin-2-yl, 1,2,3-triazol-4-yl, 1,2,4-triazol-3-yl, triazepinyl, and the like. Presently preferred moieties include those wherein A is 1,2,3-triazin-4-yl, 1,2,4-triazin-6-yl, 1,2,4-triazin-3-yl, 1,2,4-triazin-5-yl, 1,3,5-triazin-2-yl, 1,2,3-triazol-4-yl, 1,2,4-triazol-3-yl.

In accordance with still another embodiment of the invention, A is a 5-, 6-, or 7-membered ring containing, as ring members, four nitrogen atoms. Moieties contemplated for use in the practice of the invention include those wherein A is tetrazin-2-yl, tetrazin-3-yl, tetrazin-5-yl, tetrazolyl, tetrazepinyl, and the like. Presently preferred moieties include those wherein A is tetrazolyl.

In accordance with yet another embodiment of the invention, A is a 5-, 6-, or 7-membered ring containing, as ring members, one sulfur atom and two nitrogen atoms. Moieties contemplated by this embodiment of the invention include those wherein A is 1,2,6-thiadiazin-3-yl, 1,2,5-thiadiazin-3-yl, 1,2,4-thiadiazin-3-yl, 1,2,5-thiadiazin-4-yl, 1,2,3-thiadiazin-4-yl, 1,3,4-thiadiazin-5-yl, 1,3,4-thiadiazin-2-yl, 1,2,4-thiadiazin-5-yl, 1,3,5-thiadiazin-4-yl, 1,3,5-thiadiazin-2-yl, 1,2,4-thiadiazol-3-yl, 1,2,3-thiadiazol-4-yl, 1,3,4-thiadiazol-2-yl, 1,2,5-thiadiazol-3-yl, 1,2,4-thiadiazol-5-yl, thiadiazepinyl, and the like. Presently preferred moieties include those wherein A is 1,2,4-thiadiazol-3-yl, 1,2,3-thiadiazol-4-yl, 1,3,4-thiadiazol-2-yl, 1,2,5-thiadiazol-3-yl and 1,2,4-thiadiazol-5-yl.

In accordance with yet another embodiment of the invention, A is a 5-, 6-, or 7-membered ring containing, as ring members, one oxygen atom and two nitrogen atoms. Moieties contemplated by this embodiment of the invention include those wherein A is 1,2,6-oxadiazin-3-yl, 1,2,5-oxadiazin-3-yl, 1,2,4-oxadiazin-3-yl, 1,2,5-oxadiazin-4-yl, 1,2,3-oxadiazin-4-yl, 1,3,4-oxadiazin-5-yl, 1,3,4-oxadiazin-2-yl, 1,2,4-oxadiazin-5-yl, 1,3,5-oxadiazin-4-yl, 1,3,5-oxadiazin-2-yl, 1,2,4-oxadiazol-3-yl, 1,2,3-oxadiazol-4-yl, 1,3,4-oxadiazol-2-yl, 1,2,5-oxadiazol-3-yl, 1,2,4-oxadiazol-5-yl, oxadiazepinyl, and the like. Presently preferred moieties include those wherein A is 1,2,4-oxadiazol-3-yl, 1,2,3-oxadiazol-4-yl, 1,3,4-oxadiazol-2-yl, 1,2,5-oxadiazol-3-yl and 1,2,4-oxadiazol-5-yl.

In accordance with still another embodiment of the invention, A is a 5-, 6-, or 7-membered ring containing as ring members, one up to six nitrogen atoms, and/or one up to six carbon atoms, and/or zero up to five sulfur atoms, and/or zero up to five oxygen atoms.

Further, in accordance with the present invention, L is a linking moiety which links moieties A and B. L is selected from substituted or unsubstituted alkenylene moieties, alkynylene moieties or azo moieties. Presently preferred compounds of the invention are those wherein L is alkenylene or alkynylene moieties containing two carbon atoms, with alkynylene most preferred.

Further, in accordance with the present invention, B is a moiety linked through bridging moiety L to moiety A. Radicals contemplated for use in the invention are those wherein B is substituted or unsubstituted hydrocarbyl, substituted or unsubstituted cyclohydrocarbyl, substituted or unsubstituted heterocycle, optionally containing one or more double bonds, substituted or unsubstituted aryl, and the like.

Presently preferred compounds of the invention are those wherein B is a substituted or unsubstituted hydrocarbyl selected from substituted or unsubstituted alkyl moieties, alkenyl moieties, dialkenyl moieties, trialkenyl moieties, alkynyl moieties, alkadiynyl moieties, alkatriynyl moieties, alkenynyl moieties, alkadienynyl moieties, alkenediynyl moieties, and the like.

Further preferred compounds of the invention are those wherein B is a substituted or unsubstituted cyclohydrocarbyl selected from substituted or unsubstituted cycloalkyl moieties, cycloalkenyl moieties, cycloalkadienyl moieties, cycloalkatrienyl moieties, cycloalkynyl moieties, cycloalkadiynyl moieties, bicyclic hydrocarbon moieties wherein two rings have two atoms in common, and the like. Especially preferred compounds are those wherein B is cycloalkyl and cycloalkenyl having in the range of 4 up to about 8 carbon atoms.

Still further preferred compounds of the invention are those wherein B is a substituted or unsubstituted heterocycle, optionally containing one or more double bonds. Exemplary compounds include pyridyl, thiazolyl, furyl, dihydropyranyl, dihydrothiopyranyl, piperidinyl, and the like. Also preferred are compounds wherein B is substituted or unsubstituted aryl. Especially preferred compounds are those wherein substituents are methyl, trifluoromethyl and fluoro and wherein B is 3,5-di-trifluoromethyl phenyl.

Those of skill in the art recognize that invention compounds may contain one or more chiral centers, and thus can exist as racemic mixtures. For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions. Those of skill in the art will further recognize that invention compounds may exist in polymorphic forms wherein a compound is capable of crystallizing in different forms. Suitable methods for identifying and separating polymorphisms are known in the art.

As used herein, with reference to compounds not embraced by the scope of the claims, esterified carboxy is, for example, lower alkoxycarbonyl, phenyl-lower alkoxycarbonyl or phenyl-lower alkoxycarbonyl substituted in the phenyl moiety by one or more substituents selected from lower alkyl, lower alkoxy, halo and halo-lower alkyl. Esterified carboxy-lower-alkoxy is, for example, lower alkoxycarbonyl-lower alkoxy. Amidated carboxy is, for example, unsubstituted or aliphatically substituted carbamoyl such as carbamoyl, N-lower alkylcarbamoyl, N,N-di-lower alkylcarbamoyl unsubstituted or lower alkyl-, lower alkoxy-, halo- and/or trifluoromethyl-substituted N-phenyl- or N-lower-alkyl-N-phenyl-carbamoyl.

As used herein, with reference to compounds not embraced by the scope of the claims, acyl is, for example, lower alkanoyl, lower alkenoyl or unsubstituted or lower alkyl-, lower alkoxy-, halo- and/or trifluoromethyl-substituted benzoyl. Acyl amino is, for example, lower alkanoylamino, and N-acyl-N-lower alkylamino is, for example, N-lower alkanoyl-N-lower-alkylamino or unsubstituted or lower alkyl-, lower alkoxy-halo- and/or trifluoromethyl-substituted benzoylamino.

As referred to in reference to compounds not embraced by the scope of the claims "lower" groups are understood to comprise up to and including seven carbon atoms. N-lower-alkyl-N-phenylcarbamoyl is, for example, N—$C_1$–$C_4$alkyl-N-phenylcarbamoyl, such as N-methyl, N-ethyl, N-propyl, N-isopropyl or N-butyl-N-phenylcarbamoyl.

As used herein, with reference to compounds not embraced by the scope of the claims, amino-lower alkyl is, for example, amino-$C_1$–$C_4$alkyl, preferably of the formula —$(CH_2)_n$—$NH_2$ in which n is 2 or 3, such as aminomethyl, 2-aminoethyl, 3-aminopropyl or 4-aminobutyl. Hydroxy-lower alkyl is, for example, hydroxy-$C_1$–$C_4$alkyl, such as hydroxymethyl, 2-hydroxy ethyl, 3-hydroxypropyl, 2-hydroxyisopropyl or 4-hydroxybutyl. Halo-lower alkyl is, for example, polyhalo-$C_1$–$C_4$alkyl, such as trifluoromethyl.

As used herein, with reference to compounds not embraced by the scope of the claims, lower alkoxy is, for example, $C_1$–$C_7$alkoxy, preferably $C_1$–$C_4$alkoxy, such as methoxy, ethoxy, propyloxy, isopropyloxy or butyloxy, but may also represent isobutyloxy, sec.butyloxy, tert.-butyloxy or a $C_5$–$C_7$alkoxy group, such as a pentyloxy, hexyloxy or heptyloxy group.amino-lower alkoxy is, for example, amino-$C_2$–$C_4$alkoxy preferably of the formula —O—($CH_2$)$_n$ —$NR_aR_b$ in which n is 2 or 3, such as 2-aminoethoxy, 3-aminopropyloxy or 4-aminobutyloxy. Carboxy-lower-alkoxy is, for example, carboxy-$C_1$–$C_4$alkoxy, such as carboxymethoxy, 2-carboxyethoxy, 3-carboxypropyloxy or 4-carboxybutyloxy. Lower alkanoyloxy is, for example, $C_1$–$C_7$alkanoyloxy, such as acetoxy, propionyloxy, butyryloxy, isobutyryloxy or pivaloyloxy. Halo-lower alkoxy is, for example, halo- or polyhalo-$C_1$–$C_7$alkoxy, preferably halo- or polyhalo-$C_1$–$C_4$alkoxy, such as halo- or polyhaloethoxy, halo- or polyhalopropyloxy or butyl-oxy, wherein "poly" refers, for example, to tri- or pentahalo, and "halo" denotes, for example, fluoro or chloro.

As used herein, with reference to compounds not embraced by the scope of the claims, lower alkylamino-lower alkoxy is, for example, $C_1$–$C_4$alkylamino-$C_2$–$C_4$alkoxy, preferably of the formula —O—($CH_2$)$_n$— $NR_aR_b$ in which n is 2 or 3 and $R_a$ and $R_b$, independently of each other, denote lower alkyl groups as defined hereinbefore, such as methyl, ethyl, propyl or butyl. Lower alkylamino-lower alkyl is, for example, $C_1$–$C_4$alkylamino-$C_1$–$C_4$alkyl, preferably of the formula —($CH_2$)$_n$—$NR_aR_b$ in which n is 2 or 3 and $R_a$ and $R_b$, independently of each other, denote lower alkyl groups as defined hereinbefore, such as methyl, ethyl, propyl or butyl. Di-lower alkylamino-lower alkyl is, for example, Di-$C_1$–$C_4$alkylamino-$C_1$–$C_4$alkyl, preferably of the formula —($CH_2$)$_n$—$NR_aR_b$ in which n is 2 or 3 and $R_a$ and $R_b$, independently of each other, denote lower alkyl groups such as methyl, ethyl, propyl or butyl. Di-lower alkylamino-lower alkoxy is, for example, Di-$C_1$–$C_4$alkylamino-$C_2$–$C_4$alkoxy, preferably of the formula —O—($CH_2$)$_n$—$NR_aR_b$ in which n is 2 or 3 and $R_a$ and $R_b$, independently of each other, denote lower alkyl groups such as methyl, ethyl, propyl or butyl.

As used herein, with reference to compounds not embraced by the scope of the claims, optionally hydroxy-substituted lower alkyleneamino-lower alkyl is, for example, unsubstituted or hydroxy-substituted 5- to 7-membered alkyleneamino-$C_1$–$C_4$alkyl, preferably of the formula —($CH_2$)$_n$—$R_c$ in which n is 2 or 3 and $R_c$ pyrrolidino, hydroxypyrrolidino, piperidino, hydroxypiperidino, homopiperidino or hydroxyhomopiperidino. Furthermore, optionally hydroxy-substituted lower alkyleneamino-lower alkoxy is, for example, unsubstituted or hydroxy-substituted 5- to 7-membered alkyleneamino-$C_1$–$C_4$alkoxy, preferably of the formula —O—($CH_2$)$_n$—$R_c$ in which n is 2 or 3 and $R_c$ pyrrolidino, hydroxypyrrolidino, piperidino, hydroxypiperidino, homopiperidino or hydroxyhomopiperidino.

In accordance with another embodiment of the present invention, there are provided pharmaceutical compositions comprising heterocyclic compounds as described above, in combination with pharmaceutically acceptable carriers. Optionally, invention compounds can be converted into non-toxic acid addition salts, depending on the substituents thereon, Thus, the above-described compounds (optionally in combination with pharmaceutically acceptable carriers) can be used in the manufacture of medicaments useful for the treatment of a variety of indications.

Pharmaceutically acceptable carriers contemplated for use in the practice of the present invention include carriers suitable for intravenous, subcutaneous, transcutaneous, intramuscular, intracutaneous, intrathecal, inhalation, intracranial, epidural, vaginal, oral, sublingual, rectal, and the like administration. Administration in the form of creams, lotions, tablets, dispersible powders, granules, syrups, elixirs, sterile aqueous or non-aqueous solutions, suspensions or emulsions, patches, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

Invention compounds can optionally be converted into non-toxic acid addition salts. Such salts are generally prepared by reacting the compounds of this invention with a suitable organic or inorganic acid. Representative salts include hydrochloride, hydrobromide, sulfate, bisulfate, methanesulfonate, acetate, oxalate, adipate, alginate, aspartate, valerate, oleate, laurate, borate, benzoate, lactate, phosphate, toluenesulfonate (tosylate), citrate, malate, maleate, fumarate, succinate, tartrate, napsylate, methanesulfonate, 2-naphthalenesulfonate, nicotinate, benzenesulfonate, butyrate, camphorate, camphorsulfonate, cyclopentanepropionate, digluconate, dodecylsulfate, glucoheptanoate, glycerophosphate, heptanoate, hexanoate, undecanoate, 2-hydroxyethanesulfonate, ethanesulfonate, and the like. Salts can also be formed with inorganic acids such as sulfate, bisulfate, hemisulfate, hydrochloride, chlorate, perchlorate, hydrobromide, hydroiodide, and the like. Examples of a base salt include ammonium salts; alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like. Such salts can readily be prepared employing methods well known in the art.

In accordance with another embodiment of the present invention, there are provided methods for the preparation of heterocyclic compounds as described above. For example, many of the heterocyclic compounds described above can be prepared using synthetic chemistry techniques well known in the art (see *Comprehensive Heterocyclic Chemistry*, Katritzky, A. R. and Rees, C. W. eds., Pergamon Press, Oxford, 1984) from a precursor of the substituted heterocycle of Formula 1 as outlined in Scheme 1.

Scheme 1

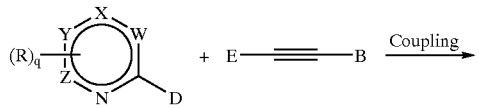

-continued

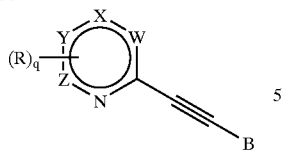

Thus in Scheme 1, a substituted heterocycle precursor (prepared using synthetic chemistry techniques well known in the art) is reacted with an alkyne derivative. In Scheme 1, $(R)_q$, W, X, Y, Z and B are as defined above and D and E are functional groups which are capable of undergoing a transition metal-catalyzed cross-coupling reaction. For example, D is a group such as hydrogen, halogen, acyloxy, fluorosulfonate, trifluoromethanesulfonate, alkyl- or arylsulfonate, alkyl- or arylsulfinate, alkyl- or arylsulfide, phosphate, phosphinate, and the like, and E is hydrogen or a metallic or metalloid species such as Li, Mgx (X is halogen), $SnR_3$, $B(OR)_2$, $SiR_3$, $GeR_3$, and the like. The coupling may be promoted by a homogeneous catalyst such as $PdCl_2(PPh_3)_2$, or by a heterogeneous catalyst such as Pd on carbon in a suitable solvent (e.g., tetrahydrofuran (THF), dimethoxyethane (DME), acetonitrile, dimethylformamide (DMF), etc.). Typically, a co-catalyst such as copper (I) iodide and a base (e.g., $NEt_3$, $K_2CO_3$ etc.) will also be present in the reaction mixture. The coupling reaction typically proceeds by allowing the reaction temperature to warm slowly from about 0° C. up to ambient temperature over a period of several hours. The reaction mixture is then maintained at ambient temperature, or heated to a temperature anywhere between 30° C. and 150° C. The reaction mixture is then maintained at a suitable temperature for a time in the range of about 4 up to 48 hours, with about 12 hours typically being sufficient. The product from the reaction can be isolated and purified employing standard techniques, such as solvent extraction, chromatography, crystallization, distillation, and the like.

Another embodiment of the present invention is illustrated in Scheme 2. A substituted heterocycle precursor is reacted with an alkene derivative in a manner similar to the procedure described for Scheme 1.

Scheme 2

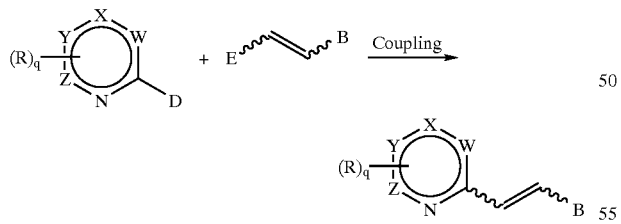

The alkene derivative product from Scheme 2 may be converted to an alkyne derivative using the approach outlined in Scheme 3.

Scheme 3

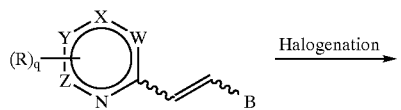

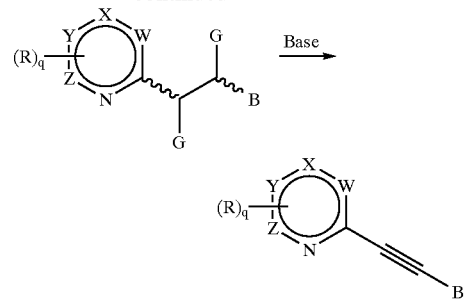

Thus, the alkene derivative may be contacted with a halogenating agent such as chlorine, bromine, iodine, NCS (N-chlorosuccinimide), NBS (N-bromosuccinimide), NIS (N-iodosuccinimide), iodine monochloride, etc. in a suitable solvent ($CCl_4$, $CHCl_3$, $CH_2Cl_2$, acetic acid, and the like). The resulting halogenated derivative (G=halogen) is then treated with a suitable base such as NaOH, KOH, DBU (1,8-diazabicyclo[5.4.0]undec-7-ene), DBN (diazabicyclononene), DABCO (1,4-diazabicyclo[2.2.2] octane), and the like, which promotes a double elimination reaction to afford the alkyne. The reaction is carried out in a suitable solvent such as ethanol, acetonitrile, toluene, etc. at an appropriate temperature, usually between about 0° C. and 150° C.

In another embodiment of the present invention, a substituted heterocyclic derivative is reacted with an aldehyde or ketone to provide a substituted alkene. (See Scheme 4.)

Scheme 4

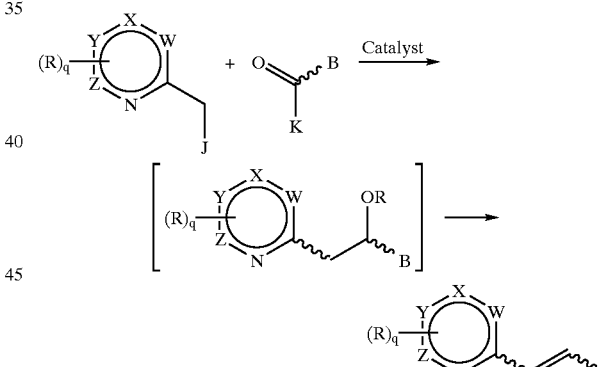

Thus, in Scheme 4, J is hydrogen, $PR_3$, $P(O)(OR)_2$, $SO_2R$, $SiR_3$, and the like, K is hydrogen, alkyl or aryl (as defined previously) and R is hydrogen, acetyl, and the like. Suitable catalysts for this reaction include bases such as NaH, n-buytllithium, lithium diisopropylamide, lithium hexamethyl disilazide, $H_2NR$, $HR_2$, $NR_3$ etc., or electropositive reagents such as $Ac_2O$, $ZnCl_2$, and the like. The reaction is carried out in a suitable solvent (THF, acetonitrile, etc.) at an appropriate temperature, usually between about 0° C. and 150° C. Sometimes an intermediate is isolated and purified or partially purified before continuing through to the alkene product.

In yet another embodiment of the present invention, a substituted heterocyclic aldehyde or ketone is reacted with an activated methylene-containing compound to provide a substituted alkene. (See Scheme 5.)

Scheme 5

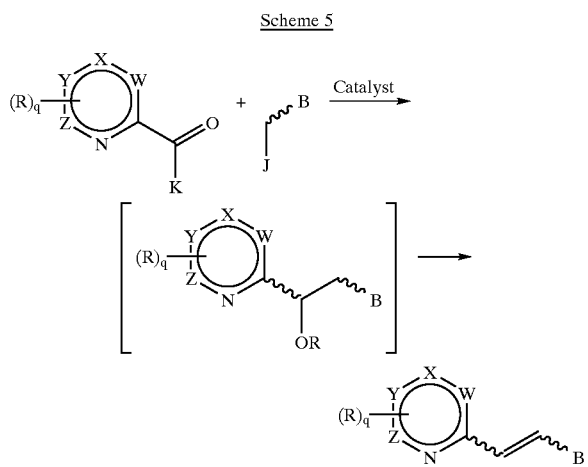

Thus, in Scheme 5, J, K, R, the catalyst and reaction conditions are as described for Scheme 4. Again, as in Scheme 4, sometimes an intermediate is isolated and purified or partially purified before continuing through to the alkene product.

The alkene products from the reactions in Scheme 4 and Scheme 5 may be converted to an alkyne derivative using reagents and conditions as described for Scheme 3.

Another method for the preparation of heterocyclic compounds of Formula I is depicted in Scheme 6.

Scheme 6

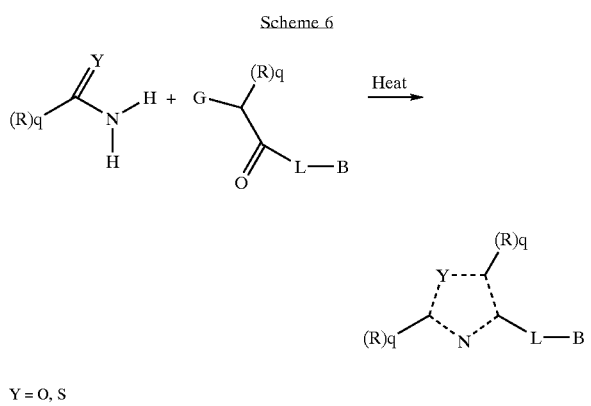

Y = O, S

In scheme 6, Y is O or S and G is halogen or a similar leaving group, and L and B are as defined previously. The reagents are contacted in a suitable solvent such as ethanol, DMF, and the like and stirred until the product forms. Typically reaction temperatures will be in the range of ambient through to about 150° C., and reaction times will be from about 1 h to about 48 h, with about 70° C. and 4 h being presently preferred. The heterocycle product can be isolated and purified employing standard techniques, such as solvent extraction, chromatography, crystallization, distillation, and the like. Often, the product will be isolated as the hydrochloride or hydrobromide salt, and this material may be carried onto the next step with or without purification.

Yet another method for the preparation of heterocyclic compounds of Formula I is depicted in Scheme 7.

Scheme 7

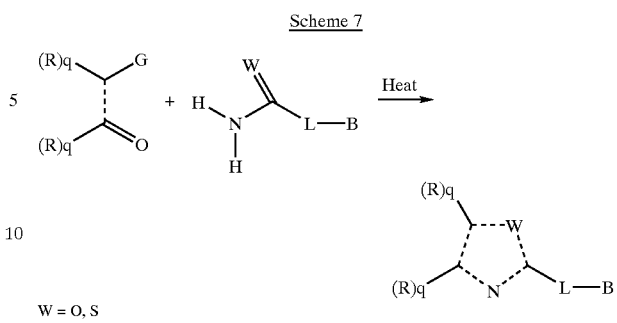

W = O, S

In Scheme 7, W may be O or S, G is halogen or a similar leaving group, and L and B are as defined previously. The reaction conditions and purification procedures are as described for Scheme 6.

In another embodiment of the present invention, depicted in Scheme 8, an alkynyl-substituted heterocycle precursor (prepared using synthetic chemistry techniques well known in the art) is reacted with a species B, bearing a reactive functional group D (See Scheme 8.)

Scheme 8

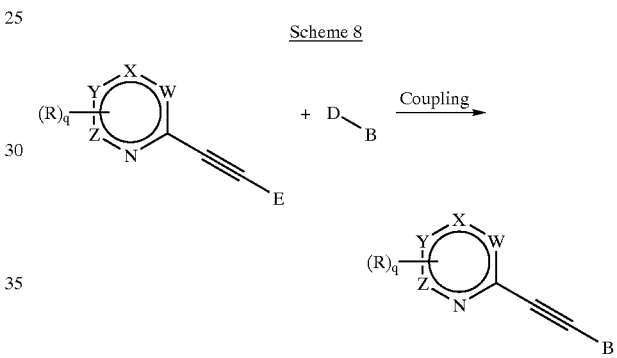

In Scheme 8, $(R)_q$, W, X, Y, Z and B are as defined above and D and E are functional groups which are capable of undergoing a transition metal-catalyzed cross-coupling reaction. For example, D is a group such as hydrogen, halogen, acyloxy, fluorosulfonate, trifluoromethanesulfonate, alkyl- or arylsulfonate, alkyl- or arylsulfinate, alkyl- or arylsulfide, phosphate, phosphinate, and the like, and E is hydrogen or a metallic or metalloid species such as Li, MgX (X is halogen), $SnR_3$, $B(OR)_2$, $SiR_3$, $GeR_3$, and the like. The coupling may be promoted by a homogeneous catalyst such as $PdCl_2(PPh_3)_2$, or by a heterogeneous catalyst such as Pd on carbon in a suitable solvent (e.g. tetrahydrofuran (THF), dimethoxyethane (DME), acetonitrile, dimethylformamide (DMF), etc.). Typically a co-catalyst such as copper (I) iodide and the like and a base (e.g. $NEt_3$, $K_2CO_3$, etc.) will also be present in the reaction mixture. The coupling reaction is typically allowed to proceed by allowing the reaction temperature to warm slowly from about 0° C. up to ambient temperature over a period of several hours. The reaction mixture is then maintained at ambient temperature, or heated to a temperature anywhere between about 30° C. up to about 150° C. The reaction mixture is then maintained at a suitable temperature for a time in the range of about 4 up to about 48 hours, with about 12 hours typically being sufficient. The product from the reaction can be isolated and purified employing standard techniques, such as solvent extraction, chromatography, crystallization, distillation, and the like.

Another embodiment of the present invention is illustrated in Scheme 9.

Scheme 9

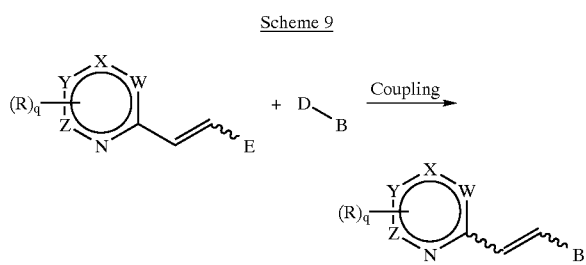

An alkenyl-substituted heterocycle precursor is reacted with an alkene derivative in a manner similar to the procedure described for Scheme 8. The product alkene derivative from Scheme 9 may be converted to an alkyne derivative using the approach outlined previously in Scheme 3 above.

In yet another embodiment of the present invention, depicted in Scheme 10, an alkynyl-substituted heterocycle precursor is reacted with a species composed of a carbonyl group bearing substituents R' and CHR"R'".

Scheme 10

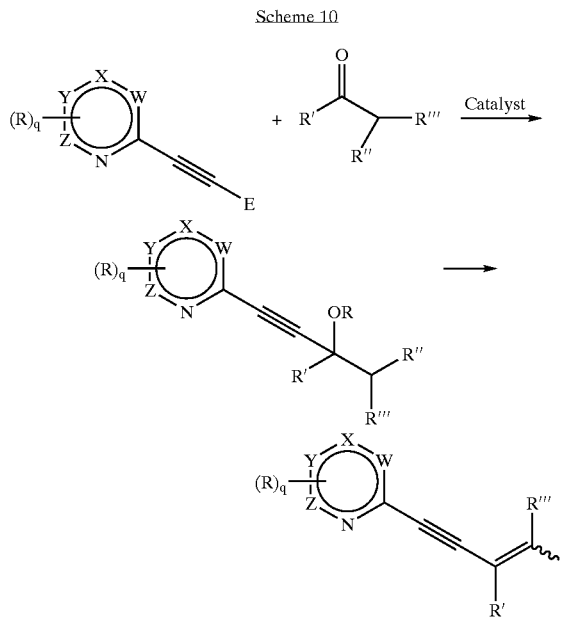

Thus in Scheme 10, R', R" and R'" may be hydrogen or other substituents as described previously, or may optionally combine to form a ring (this portion of the molecule constitutes B in the final compound). E is hydrogen or a metallic or metalloid species such as Li, MgX, wherein X is halogen, $SnR_3$, $B(OR)_2$, $SiR_3$, $GeR_3$, and the like. Suitable catalysts for this reaction include bases such as NaH, n-butyllithium, lithium diisopropylamide, lithium hexamethylsilazide, $H_2NR$, $HNR_2$, $NR_3$, $nBu_4NF$, ethylmagnesium halide, etc. R in Scheme 10 may be hydrogen, Ac, and the like. Typically the reaction is carried out in a suitable solvent such as diethylether, THF, DME, toluene, and the like, and at an appropriate temperature, usually between −100° C. and 25° C. The reaction is allowed to proceed for an appropriate length of time, usually from about 15 minutes to about 24 hours. The intermediate bearing the —OR group may be isolated and purified as described above, partially purified or carried on to the next step without purification. Elimination of the —OR group to provide the alkene derivative may be accomplished using a variety of methods well known to those skilled in the art. For example, the intermediate may be contacted with $POCl_3$ in a solvent such as pyridine and stirred at a suitable temperature, typically between about 0° C. and about 150° C., for an appropriate amount of time, usually between about 1 h and about 48 h. The product from the reaction can be isolated and purified employing standard techniques, such as solvent extraction, chromatography, crystallization, distillation, and the like.

The following examples are intended to illustrate but not to limit the invention in any manner, shape, or form, either explicitly or implicitly. While they are typical of those that might be used, other procedures, methodologies, or techniques known to those skill in the art may alternatively be used.

EXAMPLE 1

Synthesis of 2-(1-Cyclohexen-1-ylethynyl)-1,3-thiazole

Triphenylphosphine (570 mg, 2.0 mmol) was dissolved in tetrahydrofuran (THF) (20 mL), then argon was bubbled through the solution for several minutes to deoxygenate it. Palladium(II) acetate (120 mg, 0.54 mmol) was added, and the reaction mixture was heated to 60° C. for 0.5 h, and then cooled to ambient temperature. CuI (308 mg, 1.6 mmol), 2-bromo-1,3-thiazole (3.0 g, 18 mmol), 1-ethynylcyclohexene (2.4 g, 20 mmol), potassium carbonate (6 g, 45 mmol) and water (1.0 mL, 58 mmol) were dissolved in 50 mL dimethyoxyether (DME) and argon was bubbled through the solution for several minutes to deoxygenate the mixture. The catalyst solution of triphenylphosphine and palladium (II) acetate in THF was added to the reaction flask which was heated to 75° C. for 2 h. After 2 h, heating was discontinued and the reaction was allowed to cool to ambient temperature. After stirring for 16 h, gas chromatography/mass spectrometry (GC/MS) analysis showed the reaction to be complete. The mixture was filtered through Celite™, the filter pad was washed thoroughly with ethyl acetate, and the combined filtrates were concentrated in vacuo. The residue was dissolved in ethyl acetate (200 mL) and washed with water (200 mL), brine (200 mL), dried over $Na_2SO_4$, filtered, and concentrated in vacuo. The residue was purified by column chromatography eluting with hexane then 97:3 hexane:ethyl acetate to afford 2-(1-cyclohexen-1-ylethynyl)-1,3-thiazole (2.56 g, 74% yield) as a brown oil. $^1H$ NMR ($CDCl_3$, 300 MHz) δ 7.79 (d, J=3.0 Hz, 1H), 7.31 (d, J=3.0 Hz, 1H), 6.37–6.35 (m, 1H), 2.23–2.14 (m, 4H), 1.71–1.57 (m, 4H). MS (ESI) 190.0 ($M^+ + H$).

EXAMPLE 2

Synthesis of 2-Methyl-4-(1,3-thiazol-2-yl)-3-butyn-2-ol

2-Bromo-1,3-thiazole (6.0 g, 37 mmol) and CuI (1.3 g, 7.3 mmol) were combined in DME (150 mL) and argon gas was bubbled through the suspension for several minutes to deoxygenate the mixture. Triethylamine (25 mL, 180 mmol) and $PdCl_2(PPh_3)_2$ (2.5 g, 3.7 mmol) were added and 2-methyl-3-butyne-2-ol (4.6 g, 55 mmol) was added dropwise. After stirring at ambient temperature for 16 h, GC/MS showed the reaction was not complete. The reaction was heated to reflux for 2 h. The mixture was filtered through Celite™, the filter pad was washed thoroughly with ethyl acetate, and the combined filtrates were concentrated in vacuo. The residue was dissolved in ethyl acetate (600 mL), washed with water (600 mL), brine (600 mL), dried over $Na_2SO_4$, filtered and concentrated in vacuo. The residue was purified by column chromatography eluting with hexane then 7:3 hexane:ethyl acetate to afford 4-(2-thiazolyl)-2-methyl-3-butyn-2-ol contaminated with 2,7-dimethyl-but-3,5-diyne-2,7-diol. (The dimer of 2-methyl-3-butyne-2-ol) The product was crystallized from boiling hexane to afford 2-methyl-4-(1,3-thiazol-2-yl)-3-butyn-2-ol (2.18 g, 36% yield) as off white crystals that were contaminated with a small amount of 2,7-dimethyl-but-3,5-diyne-2,7-diol. M.p. 69–70° C. $^1$H NMR (CDCl$_3$, 300 MHz) δ 7.80 (d, J=3.0 Hz, 1H), 7.34 (d, J=3.0 Hz, 1H), 4.40 (s, 1H), 1.65 (s, 6H). MS (ESI) 168.1 (M$^+$+H).

EXAMPLE 3

Synthesis of 5-Chloro-3-pyridinyl trifluoromethanesulfonate

Trifluoromethanesulfonic anhydride (5.0 mL, 30 mmol) was dissolved in CH$_2$Cl$_2$ (100 mL), and cooled to 0° C. 5-Chloro-3-pyridinol (3.10 g, 23.9 mmol), and triethylamine (6.5 mL, 47 mmol) were dissolved in CH$_2$Cl$_2$ (50 mL), and the resulting solution was added to the cold trifluoromethanesulfonic anhydride solution dropwise via cannula. The resulting dark brownish-red solution was stirred at 0° C. for 5 minutes, and then the ice bath was removed and the reaction mixture was allowed to warm to ambient temperature. After stirring for 16 h at ambient temperature the reaction was quenched by pouring into water and basified by addition of saturated aqueous sodium carbonate. The basic aqueous phase was extracted with CH$_2$Cl$_2$ (2×50 mL), the combined organics dried over Na$_2$SO$_4$, filtered and concentrated in vacuo. The resulting black viscous oil was filtered through a plug of silica gel and fractions were collected while eluting with 1:1 hexane:ethyl acetate. Fractions containing the desired product were combined, concentrated in vacuo, and further purified by column chromatography eluting with 15:1 then 10:1 hexane:ethyl acetate to afford 5-chloro-3-pyridinyl trifluoromethanesulfonate (3.68 g, 59% yield) as a golden liquid. $^1$H NMR (CDCl$_3$, 300 MHz) δ 8.65 (d, J=2 Hz, 1H), 8.52 (d, J=2 Hz, 1H), 7.70 (t, J=3 Hz, 1H). MS (ESI) 261 (M$^+$, $^{35}$Cl), 263 (M$^+$, $^{37}$Cl).

EXAMPLE 4

Synthesis of 3-Chloro-5-[(trimethylsilyl)ethynyl]pyridine

5-Chloro-3-pyridinyl trifluoromethanesulfonate (4.0 g, 15 mmol) and CuI (580 mg, 3.0 mmol) were combined in DMFE (100 mL) and argon gas was bubbled through the suspension for several minutes to deoxygenate the mixture. Triethylamine (10.6 mL, 76.5 mmol), and PdCl$_2$(PPh$_3$)$_2$ (1.1 g, 1.5 mmol) were added, then trimethylsilyl-acetylene (3.3 ml, 23 mmol) was added dropwise. The reaction mixture was stirred at ambient temperature for 1 h at which time GC/MS analysis indicated that the reaction was complete. The mixture was filtered through Celite™, and the filter pad was washed thoroughly with ethyl acetate. The combined filtrates were concentrated in vacuo and the residue was dissolved in ethyl acetate (300 mL), washed with water (300 mL), brine (300 mL), dried over Na$_2$SO$_4$ filtered, and concentrated in vacuo. The residue was purified by column chromatography eluting with hexane then 99:1 hexane:ethyl acetate to afford 3-chloro-5-[(trimethylsilyl)ethynyl]pyridine (2.8 g, 87% yield) as a brown solid. $^1$H NMR (CDCl$_3$, 300 MHz) δ 8.51 (s, 1H), 8.44 (s, 1H), 7.70 (s, 1H), 0.22 (s, 9H). MS (EI ionization) 209 (M$^+$).

EXAMPLE 5

Synthesis of 3-Chloro-5-ethynylpyridine

3-Chloro-5-[(triethylsilyl)ethynyl]pyridine (1.4 g, 6.7 mmol) was dissolved in methanol (15 ml) and cooled to 0° C., to the resulting solution was added potassium carbonate (93 mg, 0.67 mmol). The ice bath was removed and the reaction mixture was stirred at ambient temperature for 0.5 h at which time thin layer chromatography (TLC) and GC/MS analysis indicated that the reaction was complete. The solvent was removed in vacuo and the residue was dissolved in diethyl ether (50 mL), washed with water (100 mL), brine (100 mL), dried over Na$_2$SO$_4$, filtered, and concentrated in vacuo to afford 3-chloro-5-ethynylpyridine (822 mg, 90% yield) which was pure by GC/MS analysis. MS (EI ionization) 137 ($^{35}$Cl M$^+$), 139 ($^{37}$Cl M$^+$). This material was carried on to the next step without further purification.

EXAMPLE 6

Synthesis of 3-Chloro-5-(1,3-thiazol-2-ylethynyl)pyridine

2-Bromo-1,3-thiazole (980 mg, 6.0 mmol) and CuI (230 mg, 1.2 mmol) were combined in DME (15 mL) and argon gas was bubbled through the suspension for several minutes to deoxygenate the mixture. Triethylamine (4.2 mL, 30 mmol) and PdCl$_2$(PPh$_3$)$_2$ (420 mg, 0.60 mmol) were added, then 3-chloro-5-ethynylpyridine (820 mg, 19 mmol) was added dropwise. After stirring at ambient temperature for 16 h, GC/MS analysis showed starting material remaining. The reaction mixture was heated at reflux for 2 h. The mixture was filtered through Celite™, the filter pad was washed thoroughly with ethyl acetate, and the combined filtrates were concentrated in vacuo. The residue was dissolved in ethyl acetate (100 mL), and washed with water (100 mL), brine (100 mL), dried over Na$_2$SO$_4$ filtered and concentrated in vacuo. The residue was purified by column chromatography eluting with hexane then 9:1 hexane:ethyl acetate to afford 3-chloro-5-(1,3-thiazol-2-ylethynyl)pyridine which contained some dimer. This material was crystallized from hot ethyl acetate to afford 3-chloro-5-(1,3-thiazol-2-ylethynyl)pyridine (300 mg 23% yield) as light orange crystals M.p. 124–125° C. $^1$H NMR (CDCl$_3$, 300 MHz) δ 8.70 (d, J=1.5 Hz, 1H), 8.59 (d, J=3.0 Hz, 1H), 7.93 (d, J=3.0 Hz, 1H), 7.88 (t, J=2.0 Hz, 1H), 7.48 (d, J=3.0 Hz, 2H). MS (ESI) 221.1 (M$^+$+H).

EXAMPLE 7

Synthesis of 2-(Cyclohexylethynyl)-1,3-thiazole

2-Bromo-1,3-thiazole (3.1 g, 19 mmol) and CuI (290 mg, 1.5 mmol) were combined in DME (30 mL) and argon gas was bubbled through the mixture for several minutes to deoxygenate the mixture. Triethylamine (13 mL, 95 mmol) and PdCl$_2$(PPh$_3$)$_2$ (530 mg, 0.76 mmol) were added and cyclohexylethyne (2.0 g, 19 mmol) was added dropwise. The reaction mixture was stirred at ambient temperature for 16 h at which time GC/MS analysis indicated that the reaction was complete. The mixture was filtered through Celite™, and the filter pad was washed thoroughly with ethyl acetate. The combined filtrates were concentrated in vacuo and the residue was dissolved in ethyl acetate (300 mL), washed with water (300 mL), brine (300 mL), dried over Na$_2$SO$_4$, filtered, and concentrated in vacuo. The residue was purified by column chromatography eluting with hexane then 99:1 hexane:ethyl acetate to afford 2-(cyclohexylethynyl)-1,3-thiazole (1.6 g, 44% yield) as a yellow oil. $^1$H NMR (CDCl$_3$, 300 MHz) δ 7.76 (d, J=9.0 Hz, 1H), 7.28 (d, J=3.0 Hz, 1H), 2.68–2.59 (m, 1H), 1.91–1.28 (m, 10H). MS (ESI) 191.7 (M$^+$).

EXAMPLE 8

2-(1-Pentynyl)-1,3-thiazole

2-Bromo-1,3-thiazole (2.0 g, 12 mmol) and CuI (183 mg, 0.96 mmol) were combined in DME (30 mL) and argon gas was bubbled through the suspension for several minutes to deoxygenate the mixture. Triethylamine (8 mL, 60 mmol) and PdCl$_2$(PPh$_3$)$_2$ (337 mg, 0.48 mmol) were added and 1-pentyne (979 mg, 14.4 mmol) was added dropwise. The reaction mixture was stirred at ambient temperature for 6 h at which time GC/MS analysis indicated that the reaction was not complete. Additional 1-pentyne (3.0 mL, 29 mmol) was added and the reaction was heated to 35° C. under a condenser. After heating for 16 h, GC/MS analysis indicated that the reaction was complete. The mixture was filtered through Celite™, and the filter pad was washed thoroughly with ethyl acetate. The combined filtrates were concentrated in vacuo and the residue was dissolved in ethyl acetate (300 mL), washed with water (300 mL), brine (300 mL), dried over Na$_2$SO$_4$ filtered, and concentrated in vacuo. The residue was purified by column chromatography eluting with hexane, 99:1, then 97:3 hexane:ethyl acetate to 2-(1-pentynyl)-1,3-thiazole (820 mg, 44% yield) as a yellow oil. $^1$H NMR (CDCl$_3$, 300 MHz) δ 7.76 (d, J=3.0 Hz, 1H), 7.28 (d, J=3.0 Hz, 1H), 2.47–2.42 (m, 2H), 1.68–1.60 (m, 2H), 1.08–0.99 (m, 3H). MS (ESI) 151.6 (M$^+$).

EXAMPLE 9

2-(3-Cyclohexyl-1-propynyl)-1,3-thiazole

2-Bromo-1,3-thiazole (2.0 g, 12 mmol) and CuI (185 mg, 0.97 mmol) were combined in DME (30 mL) and argon gas was bubbled through the suspension for several minutes to deoxygenate the mixture. Triethylamine (8.5 ml, 61 mmol) and PdCl$_2$(PPh$_3$)$_2$ (340 mg, 0.49 mmol) were added and 3-cyclohexyl-1-propyne (2.9 g, 24 mmol) was added dropwise. The reaction was stirred at ambient temperature for 16 h at which time GC/MS analysis indicated that the reaction was complete. The mixture was filtered through Celite™, and the filter pad was washed thoroughly with ethyl acetate. The combined filtrates were concentrated in vacuo. The residue was dissolved in ethyl acetate (300 mL), washed with water (300 mL), brine (300 mL), dried over Na$_2$SO$_4$, filtered, and concentrated in vacuo. The residue was purified by column chromatography eluting with hexane, then 98:2 hexane:ethyl acetate to afford 2-(3-cyclohexyl-1-propynyl)-1,3-thiazole (1.14 g, 46% yield) as a yellow oil. $^1$H NMR (CDCl$_3$, 300 MHz) δ 7.76 (d, J=3.0 Hz, 1H), 7.27 (d, J=3.0 Hz, 1H), 2.35 (d, J=6 Hz, 2H), 1.89–1.61 (m, 5H), 1.3–1.03 (m, 6H). MS (ESI) 205.9 (M$^+$+H).

EXAMPLE 10

Synthesis of 2-(1-Cyclohexen-1-ylethynyl)-5-nitro-1,3-thiazole

2-Bromo-5-nitro-1,3-thiazole (2.5 g, 12 mmol) and CuI (460 mg, 2.5 mmol) were combined in DME (30 mL) and argon gas was bubbled through the suspension for several minutes to deoxygenate the mixture. Triethylamine (8.4 mL, 60 mmol) and PdCl$_2$(PPh$_3$)$_2$ (840 mg, 1.2 mmol) were added and 1-ethynycyclohexene (1.5 g, 14.4 mmol) was added dropwise. The reaction was heated under reflux for 16 h at which time GC/MS analysis indicated that the reaction was complete. The mixture was filtered through Celite™, and the filter pad was washed thoroughly with ethyl acetate. The combined filtrates were concentrated in vacuo and the residue was dissolved in ethyl acetate (300 mL), washed with water (300 mL), brine (300 mL), dried over Na$_2$SO$_4$, filtered, and concentrated in vacuo. The residue was purified by column chromatography eluting with hexane, 99:1 then 98.5:1.5 hexane:ethyl acetate to afford 2-(1-cyclohexen-1-ylethynyl)-5-nitro-1,3-thiazole (1.4 g, 51.8% yield) as a yellow powder. M.p. 85–86° C. $^1$H NMR (CDCl$_3$, 300 MHz) δ 8.5 (s, 1H), 6.52 (br s, 1H), 2.24 (br s, 4H), 1.63 (br s, 4H). MS (ESI) 235.1 (M$^+$+H).

EXAMPLE 11

Synthesis of 2-(3,3-Dimethyl-1-butyl)-1,3-thiazole

Triphenylphosphine (380 mg, 1.5 mmol) was dissolved in THF (20 mL), then argon was bubbled through the solution for several minutes to deoxygenate it. Palladium(II) acetate (82 mg, 0.37 mmol) was added, and the reaction mixture was heated to 60° C. for 0.5 h, and then cooled to ambient temperature. CuI (210 mg, 1.1 mmol), 2-bromo-1,3-thiazole (1.6 g, 9.8 mmol), potassium carbonate (4.2 g, 31 mmol) and water (0.70 mL, 39 mmol) were dissolved in DME (30 mL) and argon was bubbled through the mixture for several minutes to deoxygenate the mixture. 3,3-dimethyl-1-butyne (1.0 g, 12.2 mmol) was then added to mixture. The catalyst solution of triphenylphosphine and palladium (II) acetate in THF was added to the reaction flask which was heated to 30° C. for 2 h. After this time heating was discontinued and the mixture was allowed to stir at ambient temperature. After stirring for 16 h, GC/MS analysis showed the reaction to be complete. The mixture was filtered through Celite™, the filter pad was washed thoroughly with ethyl acetate, and the combined filtrates were concentrated in vacuo. The residue was dissolved in ethyl acetate (200 mL), washed with water (200 mL), brine (200 mL), dried over Na$_2$SO$_4$, filtered, and concentrated in vacuo. The residue was purified by column chromatography eluting with hexane, then 99:1 hexane:ethyl acetate to afford 2-(3,3-dimethyl-1-butynyl)-1,3-thiazole (0.45 g, 28% yield) as a yellow oil. $^1$H NMR (CDCl$_3$, 300 MHz) δ 7.74 (d, J=3.0 Hz, 1H), 7.28 (d, J=3.0 Hz, 1H), 1.33 (s, 9H). MS (ESI) 166.1 (M$^+$+H).

EXAMPLE 12

Synthesis of 1-(1,3-Thiazol-2-ylethynyl) cyclopentanol

2-Bromo-1,3-thiazole (3.1 g, 19 mmol) and CuI (360 mg, 1.9 mmol) were combined in DME (30 mL) and argon gas was bubbled through the suspension for several minutes to deoxygenate the mixture. Triethylamine (13 mL, 94 mmol) and PdCl$_2$(PPh$_3$)$_2$ (660 mg, 0.94 mmol) were added and 1-ethynycyclopentanol (2.5 g, 23 mmol) was added dropwise. The reaction was heated at 50° C. for 16 h at which time GC/MS analysis indicated that the reaction was complete. The mixture was filtered through Celite™, and the filter pad was washed thoroughly with ethyl acetate. The combined filtrates were concentrated in vacuo and the residue was dissolved in ethyl acetate (300 mL), washed with water (300 mL), brine (300 mL), dried over Na$_2$SO$_4$, filtered, and concentrated in vacuo. The residue was purified by column chromatography eluting with hexane, 6:1 then 3:1 hexane:ethyl acetate to afford 1-(1,3-thiazol-2-ylethynyl)cyclopentanol (2.3 g, 52% yield) as a yellow powder. $^1$H NMR (CDCl$_3$, 300 MHz) δ 7.80 (d, J=3 Hz, 1H), 7.65 (d, J=3 Hz, 1H), 2.04–1.73 (m, 10.8H). MS (EI ionization) 193 (M$^+$).

EXAMPLE 13

Synthesis of 2-(1-Cyclopenten-1-ylethynyl)-1,3-thiazole 1-(1,3-Thiazol-2-ylethynyl)cyclopentanol was dissolved in pyridine (20 ml) and phosphorus oxychloride (1.2 g, 6.2 mmol) was added dropwise under argon. The reaction was stirred at ambient temperature for 1 h at which time a precipitate had appeared. At this time GC/MS analysis indicated that the reaction was complete and the pyridine was removed in vacuo. The residue was dissolved in ethyl acetate (200 mL) and washed with water (200 mL), brine (200 mL), dried over $Na_2SO_4$, filtered, and concentrated in vacuo. The residue was purified by column chromatography eluting with hexane then 99:1 hexane:ethyl acetate to 2-(1-cyclopenten-1-ylethynyl)-1,3-thiazole (0.25 g, 24% yield) as a light brown solid. M.p. 70.5–72° C., $^1$H NMR (CDCl$_3$, 300 MHz) δ 7.80 (d, J=3.0 Hz, 1H), 7.34 (d, J=3.0 Hz, 1H), 6.31–6.30 (m, 1H), 2.60–2.45 (m, 4H), 2.00–1.90 (m, 2H). MS (ESI) 176.1 (M$^+$+H).

EXAMPLE 14

Synthesis of Methyl 3-(1,3-thiazol-2-yl)-2-propynyl ether

2-Bromo-1,3-thiazole (2.0 g, 12 mmol) and CuI (456 mg, 2.4 mmol) were combined in DME (30 mL) and argon gas was bubbled through the suspension for several minutes to deoxygenate the mixture. Triethylamine (8.6 mL, 60 mmol) and PdCl$_2$(PPh$_3$)$_2$ (842 mg, 1.2 mmol) were added and methyl propargyl ether (1.00 g, 14.4 mmol) was added dropwise. The reaction was stirred at 55° C. under a condenser. After stirring at 55° C. for 16 h, GC/MS analysis indicated that the reaction was complete. The mixture was filtered through Celite™, and the filter pad was washed thoroughly with ethyl acetate. The combined filtrates were concentrated in vacuo and the residue was dissolved in ethyl acetate (300 mL), washed with water (300 mL), brine (300 mL), dried over $Na_2SO_4$ filtered, and concentrated in vacuo. The residue was purified by column chromatography eluting with hexane, 99:1, 97:3, then 96:4 hexane:ethyl acetate to afford methyl 3-(1,3-thiazol-2-yl)-2-propynyl ether (250 mg, 13% yield) as a yellow oil. $^1$H NMR (CDCl$_3$, 300 MHz) δ 7.78 (d, J=3.0 Hz, 1H), 7.37 (d, J=3.0 Hz, 1H), 4.37 (s, 2H), 3.47 (s, 3H). MS (ESI) 154.1 (M$^+$+H).

EXAMPLE 15

Synthesis of 2-Methyl-4-(3-pyridinyl)-3-butyn-2-ol

3-Bromopyridine (3.0 mL, 31 mmol), triethylamine (22 mL, 160 mmol), CuI (1.2 g, 6.2 mmol), and PdC$_2$(PPh$_3$)$_2$ (1.1 g, 1.5 mmol) were combined in DME (92 mL) and cooled to 0° C. 2-Methyl-3-butyne-2-ol (9.0 mL, 93 mmol) was then added and the reaction was allowed to slowly warm to ambient temperature. The mixture was then heated to 55–60° C. for 16 h. The mixture was filtered through Celite™, and the pad was washed thoroughly with ethyl acetate. The combined filtrates were washed with brine (3×100 mL), dried over MgSO$_4$, and filtered. The solution was concentrated in vacuo, and the residue was purified by column chromatography eluting with 90:10 hexane:ethyl acetate then ethyl acetate to afford 2-methyl-4-(3-pyridinyl)-3-butyn-2-ol (2.0 g; 40% yield) as a brown oil $^1$H NMR (CDCl$_3$, 300 MHz) δ 8.76 (br s, 1H), 8.52 (br s, 1H), 7.74–7.70 (m, 1H), 4.08 (br s, 1H), 1.63 (s, 3H). MS (EI ionization) 161 (M$^+$).

EXAMPLE 16

Synthesis of 3-Ethynylpyridine

2-Methyl-4-(3-pyridinyl)-3-butyn-2-ol (611 mg, 3.79 mmol) was dissolved in toluene (12 mL) at ambient temperature. A small amount (spatula tip) of NaH (60% dispersion in mineral oil) was added, and the reaction was heated to reflux. After 15 minutes the reaction was cooled to ambient temperature, and quenched by the addition of 1M aqueous HCl (30 mL). Crude product from a previous preparation (~200 mg) was added to the workup mixture. The acidic aqueous was extracted with ethyl acetate (2×20 mL), basified by the addition of saturated aqueous NaHCO$_3$, and extracted with CH$_2$Cl$_2$. The CH$_2$Cl$_2$ extracts were dried over MgSO$_4$, filtered, and concentrated in vacuo to afford crude 3-ethynylpyridine (1.5 g, >100%) as a brown liquid. $^1$H NMR (CDCl$_3$, 300 MHz) δ 8.73 (br s, 1H), 8.58 (br s, 1H), 7.80–7.76 (m, 1H), 7.29–7.16 (m, 1H), 3.28 (s, 1H). A portion of this material was carried on to the next step without further purification.

EXAMPLE 17

Synthesis of 3-(1,3-Thiazol-2-ylethynyl)pyridine

2-Bromo-1,3-thiazole (0.15 mL, 1.6 mmol), CuI (98 mg, 0.51 mmol), PdCl$_2$(PPh$_3$)$_2$ (120 mg, 0.17 mmol) and triethylamine (2.8 mL, 20 mmol) were combined in DMF (6.8 mL) and cooled in an ice bath. 3-Ethynylpyridine (520 mg, 5.04 mmol) was then added to the mixture as a solution in DMF (3.0 mL). The ice bath was removed and the reaction was allowed to stir at ambient temperature for 16 h. The reaction mixture was filtered through a pad of Celite™, and the pad was washed thoroughly with ethyl acetate. The filtrate was washed with brine (3×20 mL). A partial emulsion was observed. The mixture was concentrated in vacuo and the residue was taken up in CH$_2$Cl$_2$, washed with brine, dried over Na$_2$SO$_4$, filtered and concentrated in vacuo. The crude product was purified by column chromatography on silica gel eluting with 80:20 followed by 30:20 hexane:ethyl acetate to afford 3-(1,3-thiazol-2-ylethynyl)pyridine (160 mg) as a mixture with another product exhibiting a mass of 204 in the GC/MS, assigned as pyridylalkyne dimer. A portion of the mixture (100 mg) was further purified by preparative reverse-phase HPLC eluting with a gradient of 80:20 to 0:100 water:acetonitrile over twenty minutes. The fractions containing the desired product were collected (detection by uv at 210 nm) to afford 3-(1,3-thiazol-2-ylethynyl)pyridine as a white waxy solid (15 mg). $^1$H NMR (CDCl$_3$, 300 MHz) δ 9.3–8.5 (br s, 2H), 7.92–7.90 (m, 2H), 7.50–7.30 (m, 2H). MS (ESI) 187.0 (M$^+$+H).

EXAMPLE 18

Synthesis of 3,3,5,5-Tetramethyl-1-(2-pyridinylethynyl)cyclohexanol

To a solution of 2-ethynylpyridine (1.0 g, 10 mmol) in TMF at −78° C. was added a 1.0 M solution of ethyl magnesium bromide in THF (10 mL, 10 mmol). After stirring at reduced temperature for 30 minutes a solution of 3,3,5,5-tetramethylcyclohexanone (1.5 g, 10 mmol) in THF was added rapidly. The mixture was allowed to warm to ambient temperature over 16 hours, then partitioned between water and ethyl acetate. The organic layer was dried over anhydrous Na$_2$SO$_4$, and concentrated in vacuo. The resultant product was purified by flash column chromatography on silica gel eluting with 1:1 hexane:ethyl acetate to afford 3,3,5,5-tetramethyl-1-(2-pyridinylethynyl) cyclohexanol (250 mg, 10% yield) as a white solid. M.p. 126–127° C. $^1$H NMR (DMSO-d$_6$, 300 MHz) δ 8.57 (m, 1H), 7.64 (m, 1H), 7.39 (d, J=5 Hz, 1H), 7.22 (m, 1H), 1.91 (d, J=9 Hz, 2H), 1.71 (d, J=9 Hz, 2H), 1.26 (s, 2H), 1.14 (s, 6H), 1.09 (s, 6H).

EXAMPLE 19

Synthesis of 2-[(3,3,5,5-Tetramethyl-1-cyclohexen-1-yl)ethynyl]pyridine 3,3,5,5-Tetramethyl-1-(2-pyridinylethynyl)cyclohexanol (200 mg, 0.78 mmol) was dissolved in pyridine. $POCl_3$ (153 mg, 1.0 mmol) was added, and the mixture was heated to reflux for 6 h. After cooling, the $POCl_3$ and pyridine were removed in vacuo. The residue was purified by flash column chromatography on silica gel eluting with 2:1 hexane:ethyl acetate to afford 2-[(3,3,5,5-tetramethyl-1-cyclohexen-1-yl)ethynyl]pyridine (148 mg, 80% yield) as a light tan solid. M.p. 55–56° C. $^1$H NMR ($CDCl_3$, 300 MHz) δ 8.56 (m, 1H), 7.62 (m, 1H), 7.40 (d, J=7 Hz, 1H), 7.18 (m, 1H), 6.09 (s, 1H), 2.00 (s, 2H), 1.35 (s, 2H), 1.05 (s, 6H), 0.99 (s, 6H).

EXAMPLE 20

Synthesis of 2-[(5-Methyl-1-cyclohexen-1-yl)ethynyl]pyridine and 2-[(3-methyl-1-cyclohexen-1-yl)ethynyl]pyridine (1:1)

Using the procedures for Examples 18 and 19 but with the appropriate starting materials, 2-[(5-methyl-1-cyclohexen-1-yl)ethynyl]pyridine and 2-[(3-methyl-1-cyclohexen-1-yl)ethynyl]pyridine were obtained as a mixture of racemic regioisomers. $^1$H NMR ($CDCl_3$, 300 MHz) δ 8.56 (m, 1H), 7.62 (m, 1H), 7.40 (m, 1H), 7.19 (m, 1H), 6.32 (s, 0.5H), 6.20 (s, 0.5 H), 2.25 (m, 3H), 1.73 (m, 3H), 1.22 (m, 1H), 1.01 (m, 3H). MS (EI ionization) Two peaks: 197 ($M^+$).

EXAMPLE 21

General Procedure for 2-pyridylenynes

To a cooled a solution of 2-ethynylpyridine in THF to −78° C. was added n-BuLi (1.6 M in hexane, 1 equiv). After 20 minutes stirring at reduced temperature this material was mixed with a solution of the appropriate ketone (1 equiv) in THF. The solution was allowed to warm slowly to ambient temperature. The reaction mixture was then quenched and partitioned between water and ethyl acetate. The organic layer was dried over $Na_2SO_4$, and concentrated in vacuo. The resultant product was purified by flash column chromatography on silica gel eluting with 1:1 hexane:ethyl acetate. The resulting product was dissolved in pyridine or a mixture of pyridine and methylene chloride (1:1). $POCl_3$ (1.2 equiv) was added and the solution refluxed for 4 to 8 hours. The resultant mixture was partitioned between 1M $K_2CO_3$ and ethyl acetate. The organic layer was dried over $Na_2SO_4$, and concentrated in vacuo. The resultant product was purified by flash column chromatography on silica gel eluting with 2:1 hexane:ethyl acetate.

Using this general procedure the following example compounds (see Examples 22–33) were obtained.

EXAMPLE 22

Synthesis of 2-[(4-Methyl-1-cyclopenten-1-yl)ethynyl]pyridine and 2-[(3-Methyl-1-cyclopenten-1-yl)ethynyl]pyridine (1:1)

Reactants: 2-ethynylpyridine (620 mg, 6.0 mmol), 3-methylcyclopentanone (0.64 mL, 6.0 mmol); yields 2-[(4-methyl-1-cyclopenten-1-yl)ethynyl]pyridine and 2-[(3-methyl-1-cyclopenten-1-yl)ethynyl]pyridine (1:1) as a transparent oil (200 mg, 18% overall yield), as mixture of regio- and stereoisomers. $^1$H NMR ($CDCl_3$, 300 MHz) δ 8.56 (m, 1H), 7.64 (m, 1H), 7.44 (m, 1H), 7.20 (m, 1H), 6.19 (m, 0.5H), 6.18 (m, 0.5H), 2.90 (m, 0.5H), 2.70 (m, 2.5H), 2.21 (m, 2H), 1.48 (m, 0.5H), 1.08 (app d, J=7.5 Hz, 3H). Two peaks: 182 ($M^+$), 167 ($M^+$–Me).

EXAMPLE 23

Synthesis of 2-(Bicyclo[2.2.1]hept-2-en-2-ylethynyl)pyridine

Reactants: 2-ethynylpyridine (1.0 g, 10.0 mmol), norcamphor (1.1 g, 10.0 mmol); yields 2-(bicyclo[2.2.1]hept-2-en-2-ylethynyl)pyridine as a black oil (215 mg, 11% over two steps). This material was mixed with fumaric acid (128 mg, 1.11 mmol), dissolved in MeOH and the resulting solution was concentrated in vacuo to afford a dark brown solid. This was triturated with a mixture of ethyl acetate:ethanol (1:1) and the resultant solids were partitioned between aqueous $K_2CO_3$ and ethyl acetate. The organics were dried over $Na_2SO_4$, and concentrated in vacuo. The residue was purified by flash column chromatography on silica gel eluting with 2:1 hexane:ethyl acetate to afford 2-(bicyclo[2.2.1]hept-2-en-2-ylethynyl)pyridine (30 mg, 1.5% overall yield) as a translucent brown oil. $^1$H NMR (DMSO-$d_6$, 300 MHz) δ 8.58 (d, J=5 Hz, 1H), 7.64 (m, 1H), 7.40 (m, 1H), 7.19 (m, 1H), 6.48 (d, J=4 Hz, 1H), 3.07 (s, 1H), 2.97 (s, 1H), 1.76 (m, 2H), 1.51 (m, 1H), 1.23 (m, 1H), 1.11 (m, 1H). MS (EI ionization) 195 ($M^+$).

EXAMPLE 24

Synthesis of 2-[(2,6-Dimethyl-1-cyclohexen-1-yl)ethynyl]pyridine

Reactants: 2-ethynylpyridine (5.0 mmol, 515 mg), 2,6-dimethylcyclopentanone (6.0 mmol, 0.82 mL); yields 2-[(2,6-dimethyl-1-cyclohexen-1-yl)ethynyl]pyridine as a transparent oil (200 mg, 19% overall yield). $^1$H NMR ($CDCl_3$, 300 MHz) δ 8.56 (m, 1H), 7.60 (m, 1H), 7.42 (m, 1H), 7.19 (m, 1H), 2.40 (m, 1H), 2.10 (m, 2H), 2.01 (s, 3H), 1.76 (m, 2H), 1.56 (m, 1H), 1.34 (m, 1H), 1.22 (app d, J=7 Hz, 3H). MS (EI ionization) 211 ($M^+$).

EXAMPLE 25

Synthesis of 2-(1-Cyclohepten-1-ylethynyl)pyridine

Reactants: 2-ethynylpyridine (5.0 mmol, 515 mg), cycloheptanone (6.0 mmol, 0.71 mL); yields 2-(1-cyclohepten-1-ylethynyl)pyridine as a transparent oil (200 mg, 18% overall yield). $^1$H NMR ($CDCl_3$, 300 MHz) δ 8.54 (m, 1H), 7.59 (m, 1H), 7.40 (m, 1H), 7.16 (m, 1H), 6.52 (t, J=7 Hz, 1H), 2.47 (m, 2H), 2.26 (m, 2H), 1.77 (s, 2H), 1.61 (m, 2H), 1.56 (m, 2H). MS (EI ionization) 197 ($M^+$).

EXAMPLE 26

Synthesis of 2-(1-Cycloocten-1-ylethynyl)pyridine

Reactants: 2-ethynylpyridine (515 mg, 5.0 mmol), cyclooctanone (756 mg, 6.0 mmol); yields 2-(1-cycloocten-1-ylethynyl)pyridine as a transparent oil (250 mg, 24% overall yield). $^1$H NMR ($CDCl_3$, 300 MHz) δ 8.57 (m, 1H), 7.62 (m, 1H), 7.40 (m, 1H), 7.18 (m, 1H), 6.33 (t, J=7 Hz, 1H), 2.41 (m, 2H), 2.23 (m, 2H), 1.66 (s, 2H), 1.52 (br m, 6H). MS (EI ionization) 211 ($M^+$).

EXAMPLE 27

Synthesis of 2-[(4-Methyl-1-cyclohexen-1-yl)ethynyl]pyridine

Reactants: 2-ethynylpyridine (6.0 mmol, 618 mg), 4-methylcyclohexanone (6.0 mmol, 672 mg); yields 2-[(4- methyl-1-cyclohexen-1-yl)ethynyl]pyridine as a transparent oil (250 mg, 21% overall yield). $^1$H NMR (CDCl$_3$, 300 MHz) δ 8.57 (m, 1H), 7.59 (m, 1H), 7.39 (m, 1H), 7.20 (m, 1H), 6.30 (m, 1H), 2.22 (m, 3H), 1.72 (m, 3H), 1.25 (m, 1H), 0.99 (m, 3H). MS (EI ionization) 197 (M$^+$).

EXAMPLE 28

Synthesis of 2-(3,6-Dihydro-2H-thiopyran-4-ylethynyl)pyridine

Reactants: 2-ethynylpyridine (6.0 mmol, 618 mg), tetrahydrothiopyran-4-one (6.0 mmol, 696 mg); yields 2-(3,6-dihydro-2H-thiopyran-4-ylethynyl)pyridine as a transparent oil (150 mg, 12% overall yield). $^1$H NMR (CDCl$_3$, 300 MHz) δ 8.57 (m, 1H), 7.61 (m, 1H), 7.40 (m, 1H), 7.21 (m, 1H), 6.46 (m, 1H), 3.27 (m, 2H), 2.78 (m, 2H), 2.57 (m, 2H). MS (EI ionization) 201 (M$^+$).

EXAMPLE 29

Synthesis of 2-(3,6-Dihydro-2H-pyran-4-ylethynyl)pyridine

Reactants: 2-ethynylpyridine (6.0 mmol, 618 mg), tetrahydro-4H-pyran-4-one (6.0 mmol, 600 mg); yields 2-(3,6-dihydro-2H-pyran-4-ylethynyl)pyridine as a transparent oil (200 mg, 18% overall yield). $^1$H NMR (CDCl$_3$, 300 MHz) δ 8.57 (m, 1H), 7.63 (m, 1H), 7.44 (m, 1H), 7.21 (m, 1H), 6.29 (m, 1H), 4.25 (m, 2H), 3.81 (m, 2H), 2.36 (m, 2H). MS (EI ionization) 185 (M$^+$).

EXAMPLE 30

Synthesis of 2-{[(1R)-1,7,7-Trimethylbicyclo[2.2.1]hept-2-en-2-yl]ethynyl}pyridine Reactants: 2-ethynylpyridine (6.0 mmol, 618 mg), (1R)-(+)-camphor (6.0 mmol, 912 mg); yields 2-{[(1R)-1,7,7-timethylbicyclo[2.2.1]hept-2-en-2-yl]ethynyl}pyridine as a transparent yellow oil (125 mg, 9% overall yield). $^1$H NMR (CDCl$_3$, 300 MHz) δ 8.57 (m, 1H), 7.64 (m, 1H), 7.43 (m, 1H), 7.17 (m, 1H), 6.49 (d, J=3 Hz, 1H), 2.41 (t, J=3 Hz, 1H), 1.92 (br m, 1H), 1.65 (m, 1H), 1.18 (m, 1H), 1.17 (s, 3H), 1.09 (br m, 1H), 0.84 (s, 3H), 0.82 (s, 3H). MS (EI ionization) 237 (M$^+$).

EXAMPLE 31

Synthesis of 2-[(3,5-Dimethyl-1-cyclohexen-1-yl)ethynyl]pyridine

Reactants: 2-ethynylpyridine (6.0 mmol, 618 mg), 3,5-dimethylcyclohexanone (6.0 mmol, 0.85 mL); yields 2-[(3,5-dimethyl-1-cyclohexen-1-yl)ethynyl]pyridine as a transparent yellow oil (500 mg, 39% overall yield) as a mixture of diastereomers. $^1$H NMR (CDCl$_3$, 300 MHz) δ 8.57 (m, 1H), 7.62 (m, 1H), 7.40 (m, 1H), 7.19 (m, 1H), 6.15 (br s, 1H), 2.29 (m, 2H), 1.80 (br m, 2H), 1.00 (m, 6H), 0.88 (br m, 2H). MS (EI ionization) 211 (M$^+$).

EXAMPLE 32

Synthesis of 2-{[(5R)-5-Methyl-1-cyclohexen-1-yl]ethynyl}pyridine compound with 2-{[(3R)-3-methyl-1-cyclohexen-1-yl]ethynyl}pyridine (1:1)

Reactants: 2-ethynylpyridine (6.0 mmol, 618 mg), (3R)-(+)-3-methylcyclohexanone (6.0 mmol, 0.73 mL); yields 2-{[(5R)-5-methyl-1-cyclohexen-1-yl]ethynyl}pyridine and 2-{[(3R)-3-methyl-1-cyclohexen-1-yl]ethynyl}pyridine (1:1) as a transparent yellow oil (440 mg, 37% overall yield) as a mixture of regioisomers. $^1$H NMR (CDCl$_3$, 300 MHz) δ 8.56 (m, 1H), 7.62 (m, 1H), 7.40 (m, 1H), 7.18 (m, 1H), 6.31 (m, 0.5H), 6.19 (m, 0.5H), 2.30 (m, 3H), 1.85 (m, 2.5H), 1.22 (m, 1H), 0.98 (m, 3.5H). MS (EI ionization) 197 (M$^+$) two peaks resolved.

EXAMPLE 33

Synthesis of 2-[(3E)-3-Methyl-3-penten-1-ynyl]pyridine, 2-(3-ethyl-3-buten-1-ynyl)pyridine and 2-[(3Z)-3-methyl-3-penten-1-ynyl]pyridine Reactants: 2-ethynylpyridine (6.0 mmol, 618 mg), 2-butanone (6.0 mmol, 0.54 mL); yields 2-[(3E)-3-methyl-3-penten-1-ynyl]pyridine, 2-(3-ethyl-3-buten-1-ynyl)pyridine and 2-[(3Z)-3-methyl-3-penten-1-ynyl]pyridine as a transparent oil (135 mg, 14% overall yield) as a mixture of E, Z and exo-methylene isomers. $^1$H NMR (CDCl$_3$, 300 MHz) δ 8.59 (m, 1H), 7.65 (m, 1H), 7.44 (m, 1H), 7.20 (m, 1H), 5.88 (m, 0.75H), 5.53 (s, 0.33H) 5.40 (s, 0.33H), 2.29 (q, J=7 Hz, 0.65H), 1.93 (m, 4.5H), 1.17 (t, J=7 Hz, 1H). MS (EI ionization) 157 (M$^+$) two peaks resolved.

EXAMPLE 34

Synthesis of 5-Ethyl-2-(phenylethynyl)pyrimidine hydrochloride

2-Chloro-5-ethylpyrimidine (500 mg, 3.5 mmol), PdCl$_2$(PPh$_3$)$_2$ (250 mg, 0.35 mmol), CuI (203 mg, 1.06 mmol), triethylamine (6.0 mL, 43 mmol), and n-Bu$_4$NI (3.85 g, 10.4 mmol) were combined in dimethylformamide (DMF) (30 mL). The mixture was cooled in an ice bath and then phenylacetylene (1.5 mL, 14 mmol) was added. The reaction mixture was then heated to 45–50° C. and after 1.5 h, additional phenylacetylene (1.5 mL, 14 mmol) was added. After an additional 17 h the reaction was diluted with ethyl acetate, washed with brine (4×15 mL), dried over Na$_2$SO$_4$, filtered, and concentrated in vacuo. The resulting black oil was purified by column chromatography eluting with hexane then 90:10 hexane:ethyl acetate to afford 5-ethyl-2-(phenylethynyl)pyrimidine (770 mg, >100%) as a black oil. MS (EI ionization) 208 (M$^+$). This material was carried on to the salt formation without further purification 5-Ethyl-2-(phenylethynyl)pyrimidine (730 mg, 3.7 mmol) was dissolved in CH$_2$Cl$_2$ (3.0 mL) and treated with HCl in diethyl ether (4.1 mL of a 1N solution, 4.1 mmol). Upon addition of the HCl solution a solid precipitated from the solution. The mixture was diluted with diethyl ether (2 mL) and the supernatant decanted. The resultant solid was dried under high vacuum at 50° C. to afford 5-ethyl-2-(phenylethynyl)pyrimidine hydrochloride (450 mg, 49% yield) as an orange solid. M.p. 101–104° C. $^1$H NMR (CD$_3$OD, 300 MHz) δ 8.75 (s, 2H), 7.58–7.55 (m, 2H), 7.41–7.32 (m, 3H), 2.67 (q, J=7.6 Hz, 2H), 1.21 (t, J=7.6 Hz, 3H).

EXAMPLE 35

Synthesis of 4,6-Dimethoxy-2-(phenylethynyl)pyrimidine hydrochloride

2-Chloro-4,6-dimethoxypyrimidine (500 mg, 2.9 mmol), PdCl$_2$(PPh$_3$)$_2$ (200 mg, 0.28 mmol), CuI (160 mg, 0.84 mmol), triethylamine (4.8 mL, 34 mmol), and n-Bu$_4$NI (3.2 g, 8.7 mmol) were combined in DMF (24 mL). The mixture was cooled in an ice bath and then phenylacetylene (1.25 mL, 11.4 mmol) was added. The reaction mixture was allowed to warm to ambient temperature. After 2.5 h at ambient temperature the reaction mixture was heated to 45–50° C. After 2 h, additional phenylacetylene (1.0 mL, 9.1 mmol) was added. After an additional 17 h stirring at 45–50° C., the reaction mixture was filtered through a pad of Celite™, and the filter pad was washed thoroughly with ethyl acetate. The combined filtrates were washed with brine (4×20 mL), dried over $MgSO_4$, filtered and concentrated in vacuo. The resulting black oil was purified by column chromatography eluting with hexane, 90:10, then 85:15 hexane:ethyl acetate to afford product contaminated with an impurity. Careful column chromatography of this impure material eluting with hexane then 90:10 hexane:ethyl acetate afforded 4,6-dimethoxy-2-(phenylethynyl)pyrimidine (320 mg, 46% yield) as a yellow solid. This material was carried on to the salt formation without further purification.

4,6-Dimethoxy-2-(phenylethynyl)pyrimidine (320 mg, 1.3 mmol) was dissolved in $CH_2Cl_2$ (1.0 mL), and treated with HCl in diethyl ether (1.6 mL of a 1.0M solution, 1.6 mmol). A yellow solid precipitated immediately. The mixture was diluted with ethyl acetate and allowed to stand in the freezer for 16 h. The cold supernatant was decanted and the remaining solids were triturated with ethyl acetate (1.5 mL), and then hexane (3×2 mL). The remaining solid was dried in vacuo to afford 4,6-dimethoxy-2-(phenylethynyl) pyrimidine hydrochloride (174 mg, 47% yield) as a yellow solid. M.p. 137–138. $^1$H NMR ($CD_3OD$, 300 MHz) δ 7.65–7.62 (m, 2H), 7.46–7.42 (m, 3H), 6.16 (s, 1H), 3.97 (s, 6H).

EXAMPLE 36

Synthesis of 2-[(E)-2-(3-Fluorophenyl)ethenyl]-6-methylpyrazine 2,6-Dimethylpyrazine (5.0 g, 46 mmol) was dissolved in THF (200 mL) and cooled to 0° C. Potassium t-butoxide (46 mL of a 1.0M solution in THF, 46 mmol) was added to afford a dark red solution. The solution was allowed to warm to ambient temperature and stir for 1 hr. The solution was then cooled to 0° C., and 3-fluorobenzaldehyde (4.9 mL, 46 mmol) was added via syringe pump over 2 h. The reaction was then allowed to slowly warm to ambient temperature. After stirring at ambient temperature for 18 h, the reaction mixture was cooled to 0° C. and quenched by the addition of concentrated aqueous HCl (10 mL). The resulting suspension was allowed to warm to ambient temperature for 15 minutes, then cooled to 0° C. and brought to pH=8 by addition of solid $NaHCO_3$. The layers were separated, and the aqueous layer was extracted with ethyl acetate (3×200 mL). The combined organic layers were washed with brine (200 mL), dried over $MgSO_4$, filtered and concentrated in vacuo. The crude product was purified by column chromatography eluting with 90:10, 85:15, then 80:20 hexane:ethyl acetate to afford 2-[(E)-2-(3-fluorophenyl)ethenyl]-6-methylpyrazine (4.14 g, 42% yield) as a light yellow solid. M.p. 43–44° C. $^1$H NMR ($CDCl_3$, 300 MHz) δ 8.44 (s, 1H), 8.31 (s, 1H), 7.29 (d, J=16 Hz, 1H), 7.37–7.26 (m, 3H), 7.12 (d, J=16 Hz, 1H), 7.05–6.98 (m, 1H), 2.59 (s, 3H). MS (ESI) 214.5 ($M^+$). This material was carried on to the next step without further purification.

EXAMPLE 37

Synthesis of 2-[1,2-Dibromo-2-(3-fluorophenyl) ethyl]-6-methylpyrazine

2-[(E)-2-(3-Fluorophenyl)ethenyl]-6-methylpyrazine from Example 36 (4.14 g, 19.3 mmol) was dissolved in $CCl_4$ (40 mL). To this solution was added a solution of bromine (1.2 mL, 23 mmol) in $CCl_4$ (20 mL). The brown mixture was then heated to 60° C. After 6 h the suspension was treated with saturated aqueous $NaHCO_3$ (200 mL) and diluted with ethyl acetate (700 mL). The organic layer was washed with 5% aqueous $Na_2S_2O_3$ (100 mL), brine (100 mL), dried over $MgSO_4$, filtered, and concentrated in vacuo. The crude product was purified by column chromatography eluting with 80:20 hexane:ethyl acetate then 95:5, 94:6, and 90:10 $CH_2Cl_2$:ethyl acetate to afford 2-[1,2-dibromo-2-(3-fluorophenyl)ethyl]-6-methylpyrazine (2.97 g, 17% over two steps) as a white solid. This material was carried on to the next step without further purification.

EXAMPLE 38

Synthesis of 2-[(3-Fluorophenyl)ethynyl]-6-methylpyrazine hydrochloride

2-[1,2-Dibromo-2-(3-fluorophenyl)ethyl]-6-methylpyrazine (2.97 g, 7.94 mmol) was dissolved in THF (40 mL), treated with DBU (8.7 mL, 63 mmol), and heated to reflux. After 16 h the reaction mixture was cooled, filtered, concentrated in vacuo, and purified by column chromatography eluting with 80:20 then 75:25 hexane:ethyl acetate to afford 2-[(3-fluorophenyl)ethynyl]-6-methylpyrazine (427 mg, 25% yield). This material was carried on to the salt formation without further purification.

2-[(3-Fluorophenyl)ethynyl]-6-methylpyrazine (520 mg, 2.45 mmol) was dissolved in $CH_2Cl_2$ (3 mL), and the resulting solution was treated with HCl in diethyl ether (2.7 mL of a 1.0M solution, 2.7 mmol). The mixture was sonicated, and the solvent decanted. The remaining solid was dried under high vacuum to afford 2-[(3-fluorophenyl) ethynyl]-6-methylpyrazine hydrochloride (338 mg, 60% yield) as a light yellow solid. M.p. 62–63° C. $^1$H NMR ($CDCl_3$, 300 MHz) δ 8.73 (s, 1H), 8.57 (s, 1H), 7.54–7.35 (m, 3H), 7.28–7.20 (m, 3H), 2.84 (s, 3H).

EXAMPLE 39

Synthesis of 1-Chloro-4-(1-cyclohexen-1-yl)-3-butyn-2-one

Anhydrous $ZnCl_2$ (5.0 g, 37 mmol) was dissolved in THF (25 mL) and the solution cooled to 0° C. in an ice bath. In another flask 1-ethynylcyclohexene (4.3 mL, 36.3 mmol) was dissolved in THF (25 mL), cooled to 0° C. in an ice bath, and treated with n-butyllithium (15.7 mL of a 2.2M solution in hexane, 34.5 mmol). After 20 minutes the cyclohexenyl-ethynyllithium solution was added via cannula to the $ZnCl_2$ solution. After an additional 20 minutes $Pd(PPh_3)_4$ (620 mg, 0.54 mmol) was added to the alkynylzinc solution. The resulting yellow solution was treated with chloroacetyl chloride (4.2 mL, 55 mmol) dropwise over 10 minutes. After 2 h at 0° C. the reaction mixture was quenched by the addition of saturated aqueous $NH_4Cl$ (500 mL), and diluted with ethyl acetate. The aqueous phase was extracted with ethyl acetate (3×200 ml) and the combined organic layers were washed with water (200 ml), brine (200 ml), dried over $Na_2SO_4$, and filtered. The filtrate was concentrated in vacuo to afford a dark brown oil that was purified by column chromatography eluting with hexane, then 99:1 hexane:ethyl acetate to afford 1-chloro-4-(1-cyclohexen-1-yl)-3-butyn-2-one (4.4 g, 67% yield) as an orange oil. $^1$H NMR ($CDCl_3$, 300 MHz) δ 6.56 (m, 1H), 4.23 (s, 2H), 2.19 (m, 4H), 1.68–1.62 (m, 4H). MS (EI ionization) 182 ($^{35}Cl$ $M^+$), 184 ($^{37}Cl$ $M^+$). The material was carried on to the next step without further purification.

EXAMPLE 40

Synthesis of 4-(1-Cyclohexen-1-ylethynyl)-2-methyl-1,3-thiazole, p-toluenesulfonic acid salt 1-Chloro-4-(1-cyclohexen-1-yl)-3-butyn-2-one (2.0 g, 11.0 mmol) was dissolved in DMF (10.0 mL), thioacetamide (950 mg, 12.6 mmol) was added, and the resulting pale brown solution was stirred at ambient temperature for 64 h. The reaction mixture was diluted with ethyl acetate (300 mL), washed with saturated NaHCO$_3$ solution (300 mL), water (300 mL), brine (300 mL), dried over Na$_2$SO$_4$, filtered, and concentrated in vacuo. The residue was dissolved in ethyl acetate, adsorbed onto silica gel and purified by column chromatography eluting with hexane, 99:1 then 98:2 hexane:ethyl acetate to afford 4-(1-cyclohexen-1-ylethynyl)-2-methyl-1,3-thiazole (620 mg, 28% yield) as a yellow powder. $^1$H NMR (CDCl$_3$, 300 MHz) δ 7.22 (s, 1H), 6.27–6.24 (m, 1H), 2.7 (s, 3H) 2.22–2.12 (m, 4H), 1.68–1.58 (m, 4H).

4-(1-Cyclohexen-1-ylethynyl)-2-methyl-1,3-thiazole (620 mg, 3.1 mmol) was dissolved in ethanol (30 mL) at ambient temperature. p-Toluenesulfonic acid monohydrate (580 mg, 3.1 mmol) was added in one portion to afford a brown solution. After all of the acid had dissolved the reaction mixture was stirred for several minutes and then concentrated in vacuo to afford a dark brown oil which solidified under high vacuum. The crude material was dissolved in hot ethyl acetate. After cooling to ambient temperature the material was stored in the freezer for few hours. The supernatant solution was decanted and the crystalline solids were dried under high vacuum to afford crystalline 4-(1-cyclohexen-1-ylethynyl)-2-methyl-1,3-thiazole p-toluenesulfonate salt (882 mg, 74% yield) as yellow crystals. M.p. 128–129° C. $^1$H NMR (CD$_3$OD, 300 MHz) δ 7.87 (s, 1H), 7.71–7.68 (d, J=9 Hz, 2H), 7.24–7.21 (d, J=9 Hz, 3H), 6.38 (m, 1H), 2.88, (s, 3H), 2.36 (s, 3H), 2.21–2.17 (m, 4H), 1.68–1.64 (m, 4H).

EXAMPLE 41

Synthesis of 4-(1-Cyclohexen-1-ylethynyl)-1,3-thiazol-2-ylamine, p-toluenesulfonic acid salt 1-Chloro-4-(1-cyclohexen-1-yl)-3-butyn-2-one (2.0 g, 11 mmol) was dissolved in DMF (10.0 mL), thiourea (996 mg, 13.1 mmol) was added, and the resulting pale brown solution was stirred at ambient temperature for 16 h. The reaction mixture was diluted with ethyl acetate (200 mL), washed with saturated NaHCO$_3$ solution (100 mL), water (100 mL), brine (100 mL), dried over Na$_2$SO$_4$, filtered, and concentrated in vacuo. The dark oil was dissolved in ethyl acetate, adsorbed onto silica gel and purified by column chromatography eluting with 9:1 then 3:1 hexane:ethyl acetate to afford 4-(1-cyclohexen-1-ylethynyl)-1,3-thiazol-2-ylamine (1.1 g, 49% yield) as an off-white solid. MS (EI ionization) 204 (M+).

4-(1-Cyclohexen-1-ylethynyl)-1,3-thiazol-2-ylamine (1.1 g, 5.4 mmol) was dissolved in ethanol (40 mL) at ambient temperature. p-Toluenesulfonic acid monohydrate (1.0 g, 5.4 mmol) was added in one portion to afford a brown solution. After all of the acid had dissolved the reaction mixture was stirred for several minutes and then concentrated in vacuo to afford a dark brown oil which solidified under high vacuum. The crude material was dissolved in hot ethyl acetate. After cooling to ambient temperature the material was stored in the freezer. After several hours in the freezer, the supernatant solution was decanted and the crystalline solids were dried under high vacuum to afford 4-(1-cyclohexen-1-ylethynyl)-1,3-thiazol-2-ylamine p-toluenesulfonate salt (1.84 g, 87% yield) as off-white powder. M.p. 188–189° C. $^1$H NMR (CD$_3$OD, 300 MHz) δ 7.72–7.69 (d, J=9 Hz, 2H), 7.24–7.22 (d, J=6 Hz, 2H), 6.94 (s, 1H), 6.34–6.32 (m, 1H), 2.36 (s, 3H), 2.19–2.15 (m, 4H) 1.70–1.61 (m, 4H).

EXAMPLE 42

Synthesis of 2-(1-Cyclohexen-1-ylethynyl)-6-methylpyridine

2-Bromo-6-methyl pyridine (2.0 g, 12 mmol) and CuI (440 mg, 2.3 mmol) were combined in DME (30 mL), and argon gas was bubbled through the suspension for several minutes to deoxygenate the mixture. Triethylamine (8.0 mL, 58 mmol) and PdCl$_2$(PPh$_3$)$_2$ (814 mg, 1.16 mmol) were added, followed by the dropwise addition of 1-ethynylcyclohexene (1.7 g, 15 mmol). The reaction was stirred at ambient temperature overnight. GC/MS showed no starting 2-bromo-6-methylpyridine remaining. The mixture was diluted with ethyl acetate (100 mL), and filtered through Celite™. The pad was then thoroughly washed with ethyl acetate and the combined filtrates were washed with water (200 mL), brine (200 mL), dried over Na$_2$SO$_4$, and filtered. The filtrate was concentrated in vacuo, and the residue was purified by column chromatography eluting with hexane then 99:1, 98:2 hexane:ethyl acetate to afford 2-(1-cyclohexen-1-ylethynyl)-6-methylpyridine (1.8 g, 79% yield) as a red oil. $^1$H NMR (CDCl$_3$, 300 MHz) δ 7.51–7.46 (m, 1H), 7.21 (d, J=9 Hz, 1H), 7.03 (d, J=9 1H), 6.32–6.29 (m, 1H), 2.53 (s, 3H), 2.24–2.21 (m, 2H), 2.14–2.12 (m, 2H), 1.67–1.57 (m, 4H). MS (ESI) 198.1 (M$^+$).

EXAMPLE 43

Synthesis of 2-(Cyclohexylethynyl)-6-methylpyridine

2-Bromo-6-methyl pyridine (2.0 g, 11.6 mmol) and CuI (440 mg, 2.3 mmol) were combined in DME (30 mL), and argon gas was bubbled through the suspension for several minutes to deoxygenate the mixture. Triethylamine (8.0 mL, 58 mmol) and PdCl$_2$(PPh$_3$)$_2$ (814 mg, 1.16 mmol) were added, followed by the dropwise addition of cyclohexylethyne (1.25 g, 11.6 mmol). The reaction was stirred at ambient temperature overnight. GC/MS showed no starting 2-bromo-6-methylpyridine remaining. The mixture was diluted with ethyl acetate (100 mL), and filtered through Celite™. The pad was then thoroughly washed with ethyl acetate and the combined filtrates were washed with water (200 mL), brine (200 mL), dried over Na$_2$SO$_4$, and filtered. The filtrate was concentrated in vacuo, and the residue was purified by column chromatography eluting with hexane then 98:2, 96:4 hexane:ethyl acetate to afford 2-(cyclohexylethynyl)-6-methylpyridine (1.78 g, 77% yield) as a pale brown liquid that partially solidified on standing in the freezer. $^1$H NMR (CDCl$_3$, 300 MHz) δ 7.52–7.46 (m, 1H), 7.20 (d, J=9 Hz, 1H), 7.03 (d, J=9 Hz, 1H), 2.6 (m, 1H), 2.54 (s, 3H), 2.93–2.89 (m, 2H), 1.78–1.73 (m, 2H), 1.57–1.54 (m, 3H), 1.36–1.32 (m, 3H). MS (ESI) 200.1 (M$^+$+H).

While the invention has been described in detail with reference to certain preferred embodiments thereof, it will be understood that modifications and variations are within the spirit and scope of that which is described and claimed.

What is claimed is:

1. A compound having the structure:

A—L—B or enantiomers, diastereomeric isomers or mixtures of any two or more thereof, or pharmaceutically acceptable salts thereof, wherein:

A is 1,3-thiazol-2-yl or 1,3-thiazol-4-yl, optionally substituted with halogen, substituted or unsubstituted hydrocarbyl, substituted or unsubstituted aryl, heterocyclyl, mercapto, nitro, carboxyl, carbamido, hydroxyl, esteryl, cyano, amino, amido, or sulfonamide;

L is substituted or unsubstituted alkynylene; and

B is substituted or unsubstituted pyridyl, thiazolyl, furyl, dihydropyranyl, or dihydrothiopyranl;

wherein said substitution is by hydroxyl, alkoxy, mercapto, aryl, halogen, trifluoromethyl, pentafluoroethyl, cyano, cyanomethyl, nitro, amino, amido, carbamido, esteryl, or sulfonamide.

2. A pharmaceutical composition comprising a compound according to claim 1 and a pharmaceutically acceptable carrier therefore.

* * * * *